United States Patent
Sepke et al.

(10) Patent No.: US 7,615,109 B2
(45) Date of Patent: Nov. 10, 2009

(54) SODIUM BICARBONATE VACUUM BAG INSERTS

(75) Inventors: Arnold Sepke, Hudson, IL (US); Steven A. Bolkan, Hopewell, NJ (US); Raymond F. Ashley, Pennington, NJ (US)

(73) Assignee: Electrolux Home Care Products, Inc., Cleveland, OH (US)

( * ) Notice: Subject to any disclaimer, the term of this patent is extended or adjusted under 35 U.S.C. 154(b) by 599 days.

(21) Appl. No.: 11/417,167

(22) Filed: May 4, 2006

(65) Prior Publication Data

US 2006/0278087 A1    Dec. 14, 2006

Related U.S. Application Data

(60) Provisional application No. 60/689,255, filed on Jun. 10, 2005, provisional application No. 60/706,063, filed on Aug. 8, 2005.

(51) Int. Cl.
    *B01D 39/00* (2006.01)
(52) U.S. Cl. .................. 96/222; 55/376; 55/DIG. 2; 55/DIG. 3
(58) Field of Classification Search .................. 96/222, 96/223, 521; 55/374, 376, DIG. 2, DIG. 3
    See application file for complete search history.

(56) References Cited

U.S. PATENT DOCUMENTS

| | | | |
|---|---|---|---|
| 1,847,233 A | 3/1932 | Bilde | |
| 2,759,228 A | 8/1956 | Gordon | |
| 3,274,758 A | 9/1966 | Parman | |
| 3,452,520 A | 7/1969 | Fesco | |
| 3,971,373 A | 7/1976 | Braun | |
| 3,990,872 A | 11/1976 | Cullen | |
| 4,161,449 A | 7/1979 | Smith et al. | |
| 4,240,569 A | 12/1980 | Bessinger | |
| 4,240,813 A | 12/1980 | Fesco | |
| 4,261,849 A | 4/1981 | Benjaminson | |
| 4,440,661 A | 4/1984 | Takeuchi et al. | |

(Continued)

FOREIGN PATENT DOCUMENTS

DE        3404395        2/1984

(Continued)

*Primary Examiner*—Robert A Hopkins
(74) *Attorney, Agent, or Firm*—Hunton & Williams

(57) ABSTRACT

A vacuum cleaner bag filter with one or more filter walls forming a generally air permeable enclosure having a bag opening through it, and a flange attached to the one or more filter walls to cover the bag opening. The filter walls have a working surface area through which air can pass during use, and the flange is a relatively rigid structure having an air inlet passing into the air permeable enclosure. One or more deodorizing sheets are attached to an inner surface of the one or more filter walls. The deodorizing sheets include a first sheet layer, and sodium bicarbonate particles operatively associated with the first sheet layer. The deodorizing sheets may cover less than about 30% of the working surface area, a single deodorizing sheet may be provided, and the deodorizing sheets may be attached to the filter walls by an air impermeable adhesive that covers at least about 5% of the surface area of the deodorizing sheets. Also provided is a vacuum cleaner filter having a filter and a deodorizing sheet attached thereto by an air-impermeable adhesive.

63 Claims, 26 Drawing Sheets

U.S. PATENT DOCUMENTS

| | | | |
|---|---|---|---|
| 4,447,930 A | 5/1984 | Glenn, III et al. | |
| 4,469,734 A | 9/1984 | Minto et al. | |
| 4,476,607 A | 10/1984 | Ross | |
| 4,552,777 A | 11/1985 | Dente et al. | |
| 4,554,698 A | 11/1985 | Rennecker et al. | |
| 4,581,385 A | 4/1986 | Smith et al. | |
| 4,589,894 A | 5/1986 | Gin et al. | |
| 4,664,893 A | 5/1987 | Sarapata et al. | |
| 4,748,714 A | 6/1988 | Tschudy | |
| 4,797,318 A | 1/1989 | Brooker et al. | |
| 4,873,000 A | 10/1989 | Weller | |
| 4,948,639 A | 8/1990 | Brooker et al. | |
| 4,984,328 A | 1/1991 | Berfield | |
| 5,022,553 A | 6/1991 | Pontius | |
| 5,029,359 A | 7/1991 | Ortega | |
| 5,040,264 A * | 8/1991 | Bryant | 15/339 |
| 5,046,604 A | 9/1991 | Forhetz et al. | |
| 5,074,997 A | 12/1991 | Riley et al. | |
| 5,090,975 A | 2/1992 | Requejo et al. | |
| 5,108,470 A | 4/1992 | Pick | |
| 5,143,524 A | 9/1992 | Inculet et al. | |
| 5,181,946 A | 1/1993 | Bosses et al. | |
| 5,240,484 A | 8/1993 | Genovese et al. | |
| 5,244,703 A | 9/1993 | Bosses | |
| 5,248,323 A | 9/1993 | Stevenson | |
| 5,254,386 A | 10/1993 | Simpson et al. | |
| 5,342,420 A | 8/1994 | Bosses | |
| 5,350,443 A | 9/1994 | von Blucher et al. | |
| 5,412,837 A | 5/1995 | Worwag | |
| 5,461,751 A | 10/1995 | Sepke | |
| 5,468,447 A | 11/1995 | Bermas | |
| 5,511,278 A | 4/1996 | Shorthill | |
| 5,593,479 A | 1/1997 | Frey et al. | |
| 5,597,645 A | 1/1997 | Pike et al. | |
| 5,624,366 A | 4/1997 | Beeri | |
| 5,647,881 A | 7/1997 | Zhang et al. | |
| 5,690,711 A | 11/1997 | Bosses | |
| 5,772,959 A | 6/1998 | Bermas | |
| 5,946,770 A | 9/1999 | Bijma et al. | |
| 5,964,404 A | 10/1999 | Randolph | |
| 6,010,550 A | 1/2000 | Song | |
| 6,063,171 A | 5/2000 | Moyher, Jr. et al. | |
| 6,090,184 A | 7/2000 | Cartellone | |
| 6,099,901 A | 8/2000 | Cronia et al. | |
| 6,156,086 A | 12/2000 | Zhang | |
| 6,171,369 B1 | 1/2001 | Schultink et al. | |
| 6,171,375 B1 | 1/2001 | Howie | |
| 6,183,536 B1 | 2/2001 | Schultink et al. | |
| 6,197,096 B1 | 3/2001 | Cartellone | |
| 6,302,946 B1 | 10/2001 | Cronia et al. | |
| 6,334,881 B1 | 1/2002 | Giannetta et al. | |
| 6,358,537 B1 | 3/2002 | Hoshino et al. | |
| 6,395,046 B1 | 5/2002 | Emig et al. | |
| 6,419,729 B1 | 7/2002 | Duffy et al. | |
| 6,488,744 B2 | 12/2002 | Cartellone | |
| 6,495,097 B1 | 12/2002 | Streit et al. | |
| 6,499,183 B1 | 12/2002 | Paterson et al. | |
| 6,511,548 B1 | 1/2003 | Oreck et al. | |
| 6,514,325 B2 | 2/2003 | Cox et al. | |
| 6,524,360 B2 | 2/2003 | Cox et al. | |
| 6,555,102 B1 | 4/2003 | Hoshino et al. | |
| 6,576,601 B1 | 6/2003 | Mikic et al. | |
| 6,595,437 B1 | 7/2003 | Lawson et al. | |
| 6,630,233 B1 | 10/2003 | Levandowski et al. | |
| 6,663,306 B2 | 12/2003 | Policicchio et al. | |
| 6,716,805 B1 | 4/2004 | Sherry et al. | |
| 6,776,824 B2 | 8/2004 | Wen | |
| 6,833,342 B2 | 12/2004 | Woo et al. | |
| 6,842,936 B2 | 1/2005 | Policicchio et al. | |
| 6,994,522 B1 | 2/2006 | Chin-Chih et al. | |
| 6,997,976 B2 | 2/2006 | Fuchs | |
| 2006/0039888 A1 | 2/2006 | Yamaguti et al. | |

FOREIGN PATENT DOCUMENTS

| | | |
|---|---|---|
| DE | 3740517 | 11/1987 |
| DE | 3800252 | 1/1988 |
| DE | 3904623 | 8/1990 |
| DE | 92066614.3 | 7/1992 |
| DE | 4240172 | 11/1992 |
| DE | 4311258 | 4/1993 |
| DE | 4418720 | 5/1994 |
| DE | 4311258 C1 * | 6/1994 |
| EP | 0174273 | 8/1985 |
| EP | 860138 A1 * | 8/1998 |
| FR | 2417287 | 9/1979 |
| GB | 1094832 | 12/1967 |
| GB | 2036591 | 7/1980 |
| GB | 2268879 | 1/1994 |
| GB | 2288749 | 11/1995 |
| JP | 61 62431 | 3/1986 |
| JP | 61271013 | 12/1986 |
| JP | 05084191 | 4/1993 |
| JP | 06277168 | 10/1994 |
| JP | U-07039740 | 2/1995 |
| WO | WO 94/21305 | 9/1994 |
| WO | WO 01/08543 | 2/2001 |

* cited by examiner

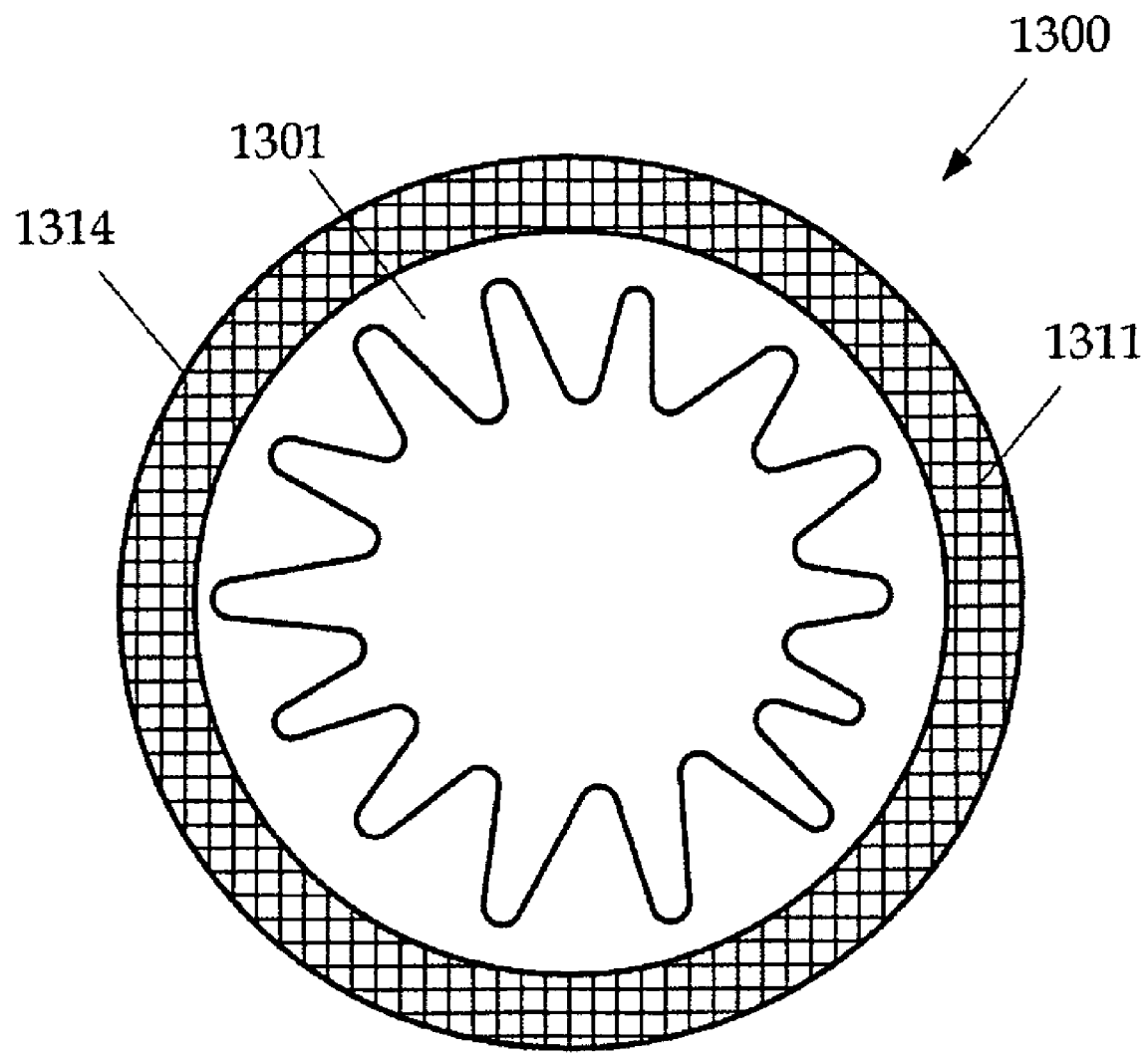

SODIUM BICARBONATE VACUUM BAG INSERTS

The present application claims priority to provisional application 60/689,255, filed on Jun. 10, 2005 and provisional application 60/706,063, filed on Aug. 8, 2005. Both of these provisional applications are incorporated herein by reference in their entirety.

FIELD OF THE INVENTION

The present invention relates to vacuum cleaners, central vacuum cleaners, extraction cleaning devices, and other cleaning appliances having chemical neutralizing features.

BACKGROUND OF THE INVENTION

Many types of cleaning devices are available for commercial and consumer cleaning needs. For example, conventional vacuums are often used for general floor cleaning, central vacuum systems have been developed for a convenient means of general floor cleaning, various types of extraction cleaners have been developed to provide deeper or more problem-specific carpet and upholstery cleaning, and cleaning wands having dry or moistened disposable wipes are used for quickly cleaning hard surfaces.

A common problem among these and other cleaning appliances is that they often pick up or develop odors from the substances that they clean off the floor. Such odors can make it undesirable to operate or clean the appliance, or give the perception that the cleaning appliance is not cleaning effectively, and result in customer dissatisfaction with the device. These odors may also present a perceived health risk.

Various attempts have been made to address the accumulation of odors in cleaning appliances. For example, U.S. Pat. No. 5,461,751, which is incorporated herein by reference, discloses a vacuum cleaner having a cedar insert in the vacuum bag that acts as an air freshener and pesticide. In another device, shown in International Patent Publication WO 01/08543 A1, an adsorbent material such as activated carbon is introduced into a vacuum dust filter bag. While the foregoing developments have been useful for controlling or masking odors, they have not conclusively solved the problem of lingering odors in cleaning appliances and preventing odors on surfaces being cleaned.

In view of these and other problems, there remains a need to provide improved methods and apparatuses for controlling odors in cleaning appliances.

SUMMARY OF THE INVENTION

One aspect of the present invention provides a vacuum cleaner bag filter having one or more filter walls forming a generally air permeable enclosure having a bag opening therethrough, and a flange attached to the one or more filter walls to cover the bag opening. The filter walls have a working surface area through which air can pass during use, and the flange has a relatively rigid structure having an air inlet passing into the air permeable enclosure. A deodorizing sheet, which may comprise a single sheet or multiple sheets, is attached to an inner surface of the filter walls. The deodorizing sheet includes a first sheet layer, and a plurality of sodium bicarbonate particles operatively associated with the first sheet layer. In this first aspect of the invention, the deodorizing sheet covers less than about 30% of the working surface area.

Another aspect of the invention provides a vacuum cleaner bag filter having one or more filter walls forming a generally air permeable enclosure having a bag opening therethrough, and a flange attached to the one or more filter walls to cover the bag opening. The filter walls have a working surface area through which air can pass during use, and the flange has a relatively rigid structure having an air inlet passing into the air permeable enclosure. A deodorizing sheet is attached to an inner surface of the filter walls. The deodorizing sheet includes a first sheet layer, and a plurality of sodium bicarbonate particles operatively associated with the first sheet layer. In this first aspect of the invention, a single deodorizing sheet is installed in the vacuum cleaner bag.

Yet another aspect of the invention provides a vacuum cleaner bag filter having one or more filter walls forming a generally air permeable enclosure having a bag opening therethrough, and a flange attached to the one or more filter walls to cover the bag opening. The filter walls have a working surface area through which air can pass during use, and the flange has a relatively rigid structure having an air inlet passing into the air permeable enclosure. One or more deodorizing sheets are attached to an inner surface of the filter walls. The one or more deodorizing sheets include a first sheet layer, and a plurality of sodium bicarbonate particles operatively associated with the first sheet layer. In this first aspect of the invention, the one or more deodorizing sheets are attached to the filter walls by an air impermeable adhesive that covers at least about 5% of the total surface area of the deodorizing sheets.

Still another aspect of the invention provides a vacuum cleaner filter having a generally air permeable filter with a first filter side and a second filter side. The filter is adapted to fit into a vacuum cleaner such that a first filter side faces an incoming air stream, and second filter side is opposite the first side. A deodorizing sheet is attached to the filter on at least one of the first filter side and the second filter side. The deodorizing sheet includes a first sheet layer, and a plurality of sodium bicarbonate particles operatively associated with the first sheet layer. The deodorizing sheet is attached to the filter by an air impermeable adhesive that covers more than about 5% of the total surface area of the deodorizing sheet.

Other uses and variations on the foregoing will be apparent to one of ordinary skill in the art after studying the present disclosure and practicing the invention described herein.

BRIEF DESCRIPTION OF THE DRAWINGS

FIG. 13C is a variation of the embodiment of FIG. 13A.

DETAILED DESCRIPTION OF THE PREFERRED EMBODIMENTS

The present invention provides methods and apparatuses for neutralizing odors in cleaning appliances, such as vacuum cleaners, central vacuum systems, extractors, and cleaning wands. The methods and apparatuses preferably use sodium bicarbonate, a non-toxic and non-irritating substance having the chemical formula $NaHCO_3$, and often referred to as baking soda. Sodium bicarbonate is a known compound, and is generally provided as a white, powdered substance, but it is also known to form it into a solid form or a liquid slurry. It is in widespread use as a cooking additive, for acid reduction, and as a mild abrasive for cleaning. Sodium bicarbonate also acts as a deodorizer by neutralizing the acidic or basic components of odors and turning them into non-volatile salts. Various commercial products have been developed to use sodium bicarbonate in refrigerators and on carpets to reduce odors produced by foods, pets, smoke, and other sources. An example of a product that is used for deodorizing carpets is sold under the name ARM & HAMMER CARPET AND ROOM DEODORIZER, which is available from Church & Dwight Co., Inc., of Princeton, N.J. This product is generally deposited by hand on a carpet, and removed with a conventional vacuum cleaner.

Referring to the included Figures, in a first embodiment, the present invention provides a sodium bicarbonate chemical neutralizer that is used in conjunction with a vacuum cleaner 100 having a bag-type dirt filter 102. Numerous variations of this embodiment are envisioned, and for ease of illustration a number of these variations are shown on a single vacuum cleaner 100 in FIG. 1. It is believed that any one of the various employments of sodium bicarbonate neutralizers shown in FIG. 1 may be sufficient to obtain favorable odor neutralization, and therefore the invention contemplates and encompasses the use of any combination of one or more of these variations with a bag filter-type vacuum cleaner.

Figure 1:
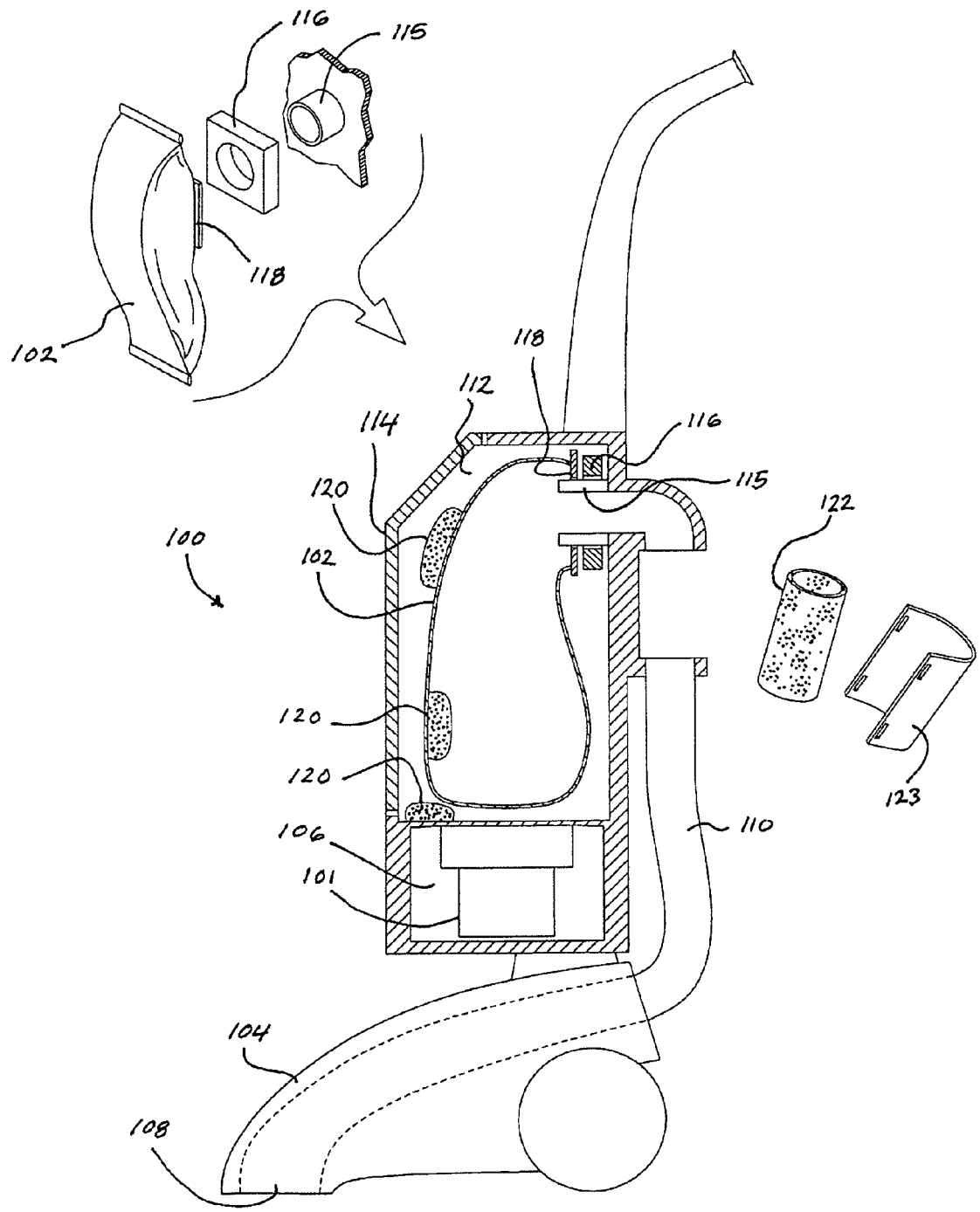
FIG. 1 is a first set of embodiments of the present invention shown in conjunction with a bag vacuum cleaner.

The vacuum cleaner of FIG. 1 is generally of conventional construction, and includes a floor-contacting base 104 to which an upright rear housing 106 is pivotally attached. The rear housing 106 can be positioned in an upright resting position and leaned back for use in guiding the base 104 across the surface being cleaned, as known in the art. The base includes an inlet nozzle 108, which may have a rotatable agitator (not shown) mounted therein.

The nozzle 108 is connected to the filter bag 102 by an inlet conduit 110. A typical inlet conduit 110 comprises a series of rigid and/or flexible tubes. All or a portion or the conduit 110 may be transparent to help locate clogs, and a portion of the conduit 110 may be removable to assist with cleaning clogs therefrom. An example of a conduit 110 having a transparent, removable portion is shown in U.S. Pat. No. 5,991,791, which is incorporated herein by reference. The inlet conduit 110 may be detachable from the base 104 for use as an above-floor cleaning hose, or may include a valve that cuts off airflow from the inlet 108 and redirects the airflow to a separate above-floor cleaning hose. Such devices are known in the art.

A conventional fan and motor assembly 101 is used to generate a vacuum to draw dirt-laden air into the nozzle 108, through the conduit 110, and into the dust bag 102. The fan may be fluidly located at some point in the conduit 110 to convey the dirt-laden air to the filter bag 102 under positive pressure, or may be located downstream of the filter bag 102 to draw dirt-laden air into the filter bag 102 under a vacuum. The second alternative is shown in FIG. 1. Additional filters may also be provided in the conduit 110 or at locations downstream of the filter bag 102 to provide additional dirt filtration and air cleaning.

The filter bag 102 is located within a bag chamber 112 on the rear housing 106, which is covered by a suitable lid 114. The chamber 112 and lid 114 may optionally be replaced by an air-permeable fabric cover as may be desired when the fan is positioned to convey the air into the filter bag 102 under pressure. The filter bag 102 is releasably mounted to the end of the conduit 110 by a mounting tube 115 that fits into a corresponding mounting flange 118 on the filter bag 102. This type of bag mounting arrangement is known in the art, and shown, for example, in U.S. Pat. Nos. 4,119,414; 6,217,641; and 6,484,352, which are incorporated herein by reference. A lock-out device (not shown) may be provided to prevent operation of the vacuum cleaner 100 or closure of the lid 114 without the presence of the filter bag 102.

Other features and accessories of the vacuum cleaner 100 will be understood by those of ordinary skill in the art, and the invention is not intended to be limited to any particular construction. Non-limiting examples of typical vacuum cleaners and features that can be used with the present invention are shown in U.S. Pat. Nos. 4,376,322; 5,309,361; 6,122,796; and 6,308,374, which are incorporated herein by reference. Furthermore, while the embodiments of FIG. 1 are described with reference to a conventional upright vacuum cleaner, they may be used in generally the same manner in vacuums having different configurations, such as canister or stick-type vacuums, central vacuums, and the like. Non-limiting examples of such vacuums include those shown in U.S. Pat. Nos. 5,701,631 and 5,813,085, which are incorporated herein by reference. The changes to the designs set forth above required to use the invention in these different vacuum configurations will be apparent to those of ordinary skill in the art.

The vacuum cleaner 100 of FIG. 1 is provided with various sodium bicarbonate neutralizing structures. A first such structure is in the form of an air-pervious bag or sachet 120 filled with sodium bicarbonate. The sachet 120 may be located within the filter bag 102, on the outside of the filter bag 102, or within the filter bag compartment 112. The sachet 120 may also be located on the interior or exterior of the filter bag fabric cover, if one is used. In this embodiment, the sachet 120 may be provided as a separate device as an aftermarket odor-neutralizing additive that can be used with any vacuum cleaner. In this case, the sachet 120 may be simply placed in the desired location, or may be provided with an adhesive backing or clips to hold it in place. The sachet 120 may alternatively be sewn into or formed as part of the filter bag 102. For example, when formed as part of the filter bag, the sachet 120 may be formed by creating a fold in the filter bag material, filling the fold with sodium bicarbonate, and sewing or bonding the fold shut so that the sodium bicarbonate is captured therein. Other examples of such embodiments are described elsewhere herein.

In another embodiment, a slurry of sodium bicarbonate is printed or painted onto the filter bag material before or after it is formed into the filter bag 102. The sodium bicarbonate may also be provided in a powdered form that is captured between layers of the filter bag 102. A particular advantage these embodiments is that the supply of sodium bicarbonate is renewed whenever the filter bag 102 is replaced. In either of these embodiments, it is believed that the amount of sodium bicarbonate can be adjusted so that it provides odor neutralization, while not unduly reducing the permeability of the filter bag 102. For example, if the sodium bicarbonate is painted on the filter bag 102, this may be done so in stripes or other patterns that leave portions of the filter bag 102 in their original, porous state. When capturing the sodium bicarbonate between the layers of the filter bag, the basis weight of the sodium bicarbonate can be adjusted to minimize any detrimental effects on the bag's porosity.

In another embodiment, an odor neutralizing structure of sodium bicarbonate is formed as a rigid sleeve 122 that fits within the inlet conduit 110. In this embodiment, the conduit 110 can be selectively opened or detached to allow the sleeve 122 to be inserted therein. As the incoming dirt-laden air passes through the conduit 110 and the sleeve 122, the sleeve 122 gradually erodes, thus providing controlled distribution of the sodium bicarbonate into the filter bag 102, where it can react with the collected matter to neutralize offensive odors. The sleeve 122 may be located within a transparent, removable portion of the conduit 123 to assist the user in determining when the sleeve 122 is at or near the end of its useful life.

In a variation of this embodiment, the sodium bicarbonate my be adhered to the interior walls of a portion of the conduit 110, rather than provided as a replaceable sleeve 122. In this embodiment, the portion of the conduit 110 to which the sodium bicarbonate is adhered may be provided as a replacement part for use when the original supply is fully eroded, or adhesive-backed inserts may be provided as replacements.

The sodium bicarbonate may also be molded into a rigid insert 116 that fits over or within the bag mounting tube 115. In this embodiment, the insert 116 is installed on or in the mounting tube 115 whenever a new bag is placed in the device, or whenever the insert becomes sufficiently eroded. The sodium bicarbonate may also be formed as a tube that serves as the mounting tube 115 itself. An advantage of this construction is that the consumer is not able to mount the filter bag 102 and operate the device without the sodium bicarbonate form being present.

Figure 2A:
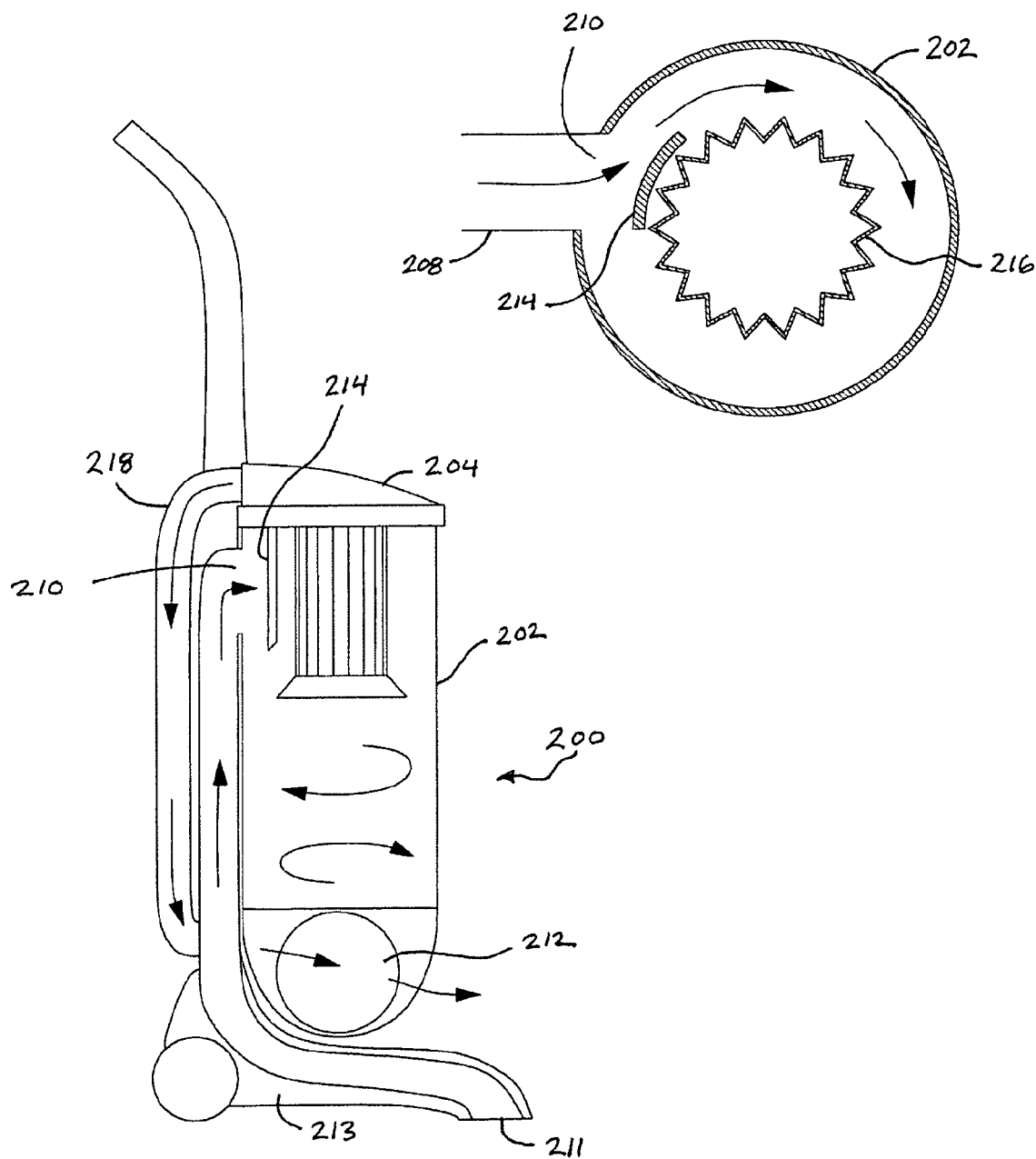
FIG. 2A illustrates schematic views of an exemplary bagless vacuum cleaner of the present invention showing the air flow path therein.
Figure 2B:
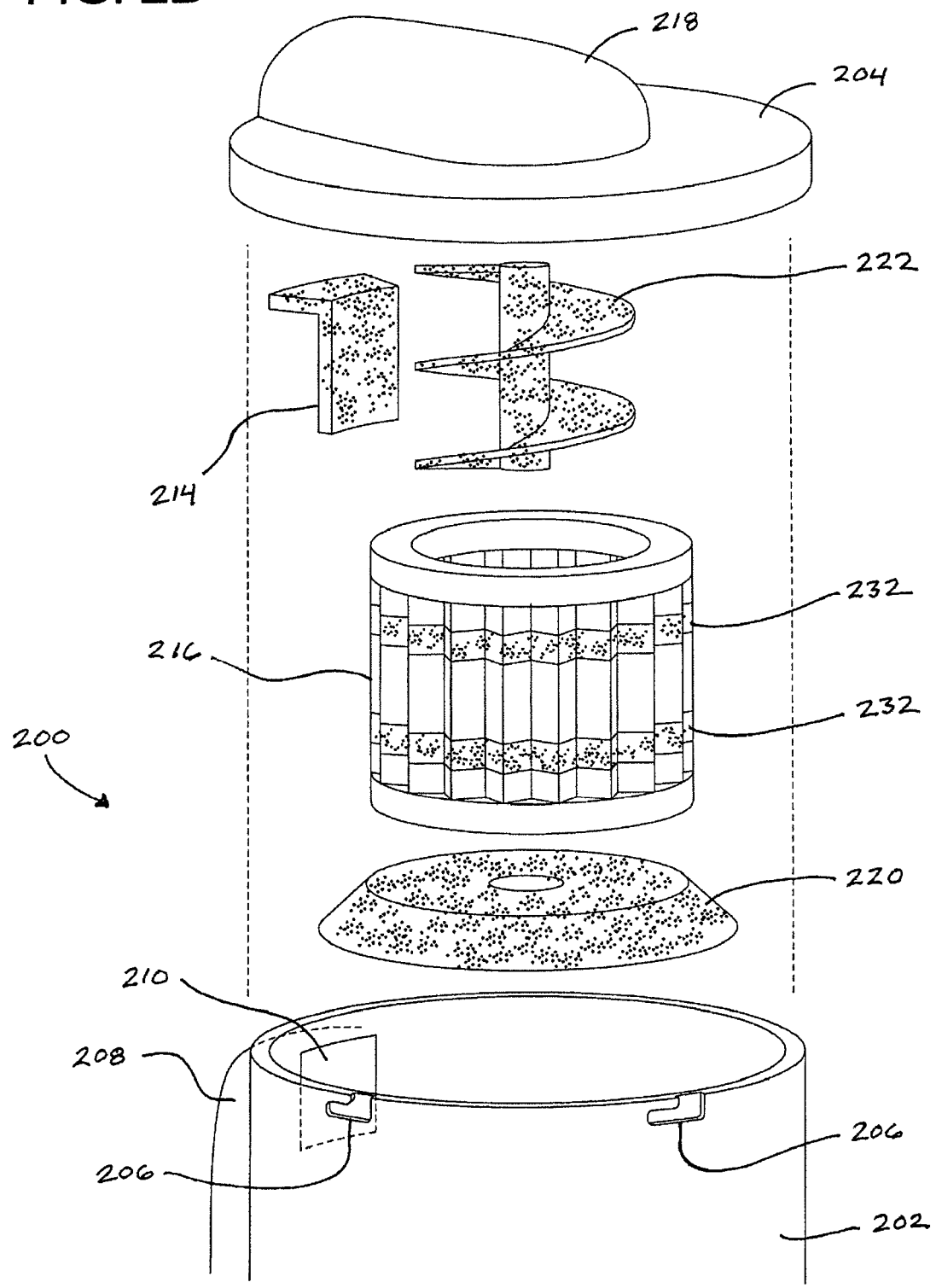
FIG. 2B is a first set of embodiments of the present invention shown in conjunction with the exemplary bagless vacuum cleaner of FIG. 2A.
Figure 2C:
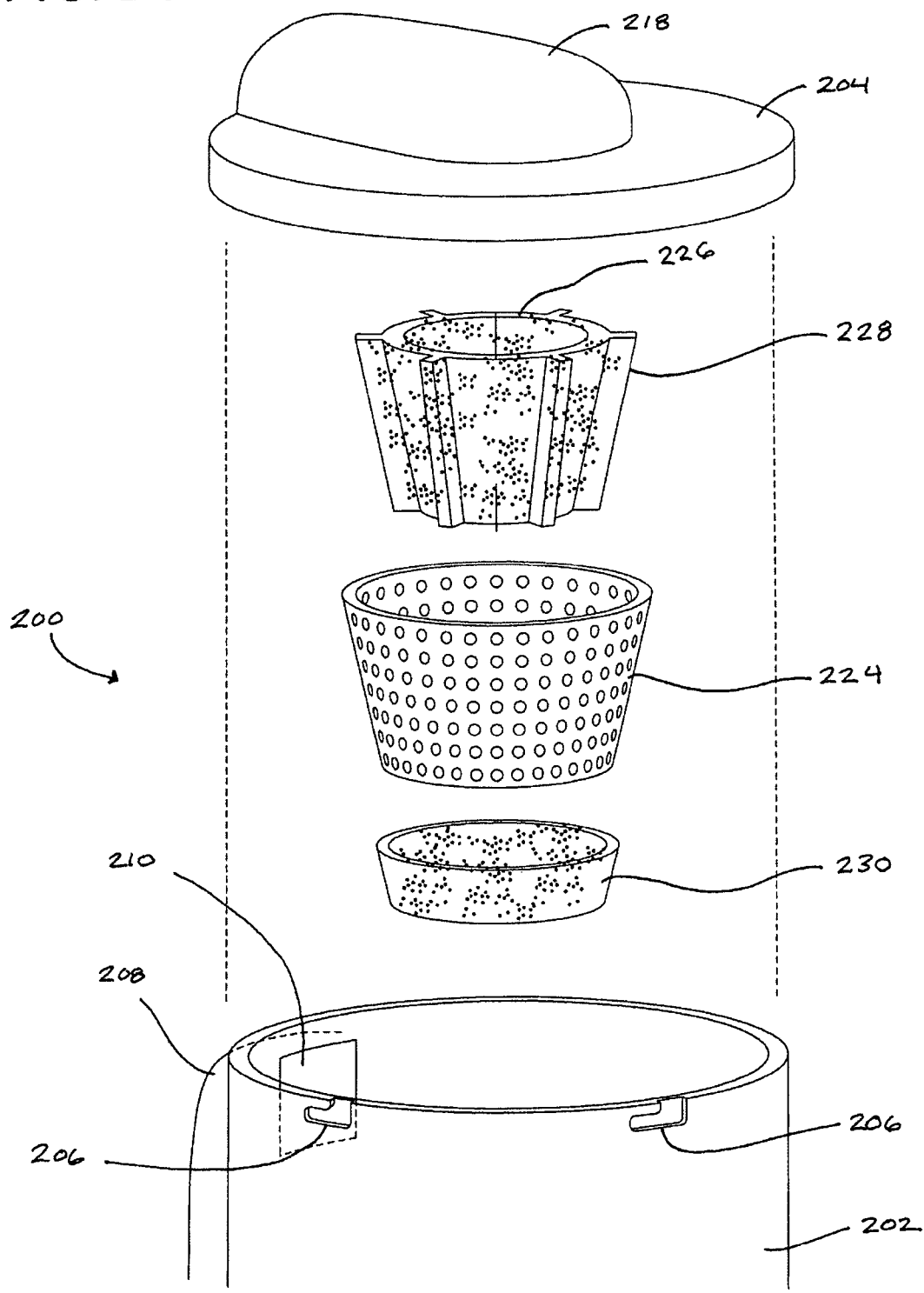
FIG. 2C is a second set of embodiments of the present invention shown in conjunction with the exemplary bagless vacuum cleaner of FIG. 2A.

Referring now to FIGS. 2A-2C, the present invention also may be used with bagless vacuums, such as those that use a dust cup, rather than a filter bag. Non-limiting examples of various other canister and upright bagless vacuums that may be used with the present invention include those shown in U.S. Pat. Nos. 4,665,582; 6,168,641; 6,311,366; 6,502,277; and 6,863,702, which are incorporated herein by reference. FIG. 2A illustrates side and top cutaway views of a typical upright bagless vacuum cleaner that may use the present invention. FIGS. 2B and 2C illustrate two sets of embodiments of the present invention that may be used with the vacuum cleaner of FIG. 2A, or other vacuums, such as stick or canister vacuums. A number of variations of this embodiment are shown on a single bagless dust cup in FIGS. 2B and 2C, but any one or more of the various employments of sodium bicarbonate neutralizers shown in FIGS. 2B and 2C may be used with a bagless vacuum cleaner on its own or in other combinations.

The bagless dustcup 200 of FIG. 2A comprises a dirt receptacle 202 to which a lid 204 is attached by bayonet fittings 206, threaded engagement, compression fitting, or other known attachment devices. The dirt receptacle 202 preferably is made of a transparent plastic material, or with a transparent window, so that its contents can be readily examined. The dirt receptacle 202 has a dirty air inlet passage 208 that opens into the dirt receptacle 202 at an inlet opening 210. Air is drawn into the dirty air inlet passage 208 through an inlet nozzle 211 in a base assembly 213 by a vacuum motor 212. As the incoming dirt-laden air enters the dirt receptacle 202, it is forced into a swirling, centrifuging motion by a deflector plate 214 located adjacent the opening 210. This centrifuging motion separates larger particles from the air in the manner of conventional cyclonic separators, and the partially-cleaned air exits the dirt receptacle 202 through a pleated filter 216. The exiting air passes through an outlet passage 218 in the lid 204, and then to the vacuum motor 212. Alternatively, the outlet passage 218 may extend downward and exit through the bottom of the dirt cup 200, as known in the art.

Sodium bicarbonate odor neutralizers can be integrated into the dirt cup 200 in a number of ways, but are preferably provided as sacrificial solid forms of sodium bicarbonate that are located in the airstream such that they are gradually eroded by the air flowing through the device, or as sodium bicarbonate-impregnated filter elements located within the dirt cup 200. In a first embodiment, shown in FIG. 2B, the sodium bicarbonate is molded to form (or be attached to) the inlet deflector plate 214. In this embodiment, the incoming airstream strikes the deflector plate 214, causing gradual erosion of the solid sodium bicarbonate. The freed sodium bicarbonate is expected to mix with the contents of the airstream in a uniform manner, and thereby chemically neutralize odors of the material in the airstream. The remaining solid sodium bicarbonate and the eroded sodium bicarbonate also help neutralize odors present in the dustcup 200 when the device is not in use. In this embodiment, the sodium bicarbonate deflector plate 214 (or the sodium bicarbonate attachment thereto) can be replaced periodically as it erodes.

In another embodiment, also shown in FIG. 2B, the pleated filter 216 may include a reverse airflow deflector 220 that is attached to the bottom of the filter 216. This reverse flow deflector 220 may be formed of a solid sodium bicarbonate material that gradually erodes and neutralizes odors in the dustcup, as described above. In still another embodiment in FIG. 2B, an insert 222 made of a solid sodium bicarbonate material may be provided in the filter 216. This insert 222 may take the form of a simple sleeve or pellet(s). The insert 222 may also be shaped to create a tortuous or spiraling airflow path that causes the air exiting the filter to pass across its surface to thereby release sodium bicarbonate from the insert 222. For example, the shown insert 222 is shown having an auger-like shape that forces the air to cross a relatively large sodium bicarbonate surface area before exiting the device. The insert 22 may alternatively comprise a powder in an air-permeable sachet, as described previously herein, a sodium bicarbonate impregnated air permeable sheet, as described later herein, or other device.

The pleated filter 216 of the embodiment of FIG. 2B may also be provided with a pattern of sodium bicarbonate, which can be impregnated into the filter material itself, or painted or printed onto the filter medium before or after it is formed into a pleated filter 216. In the shown embodiment, two sodium bicarbonate strips 232 are applied to the pleated filter 216. The amount of sodium bicarbonate applied to the filter in this manner preferably has sufficient mass to provide odor neutralization in the dirt receptacle 202, but is not so great that it unduly reduces the efficiency of the filtration process. Blockage of up to 20% or more may be allowable, depending on the total filter area and the filtration requirements of the vacuum cleaner.

Other embodiments of the invention do not include a pleated filter 216. For example, the filter 216 may be replaced by a conical or cylindrical perforated or screen cyclone center 224, as shown in FIG. 2C. In this embodiment, a solid sodium bicarbonate insert 226 may be provided within the cyclone insert so that air entering the cyclone insert strikes the insert 226. Ribs 228 on the insert 226, or more preferably on the inner surface of the cyclone center 224 (not shown), keep the sodium bicarbonate insert 226 from blocking airflow through the cyclone center 224. The cyclone center 224 may also have a solid or perforated sodium bicarbonate sleeve 230 positioned on its exterior surface to contact the air swirling around the cyclone center 224.

Other variations on sacrificial, renewable sodium bicarbonate inserts and other forms will be apparent to those of ordinary skill in the art in view of the present disclosure and with practice of the invention.

Figure 3A:
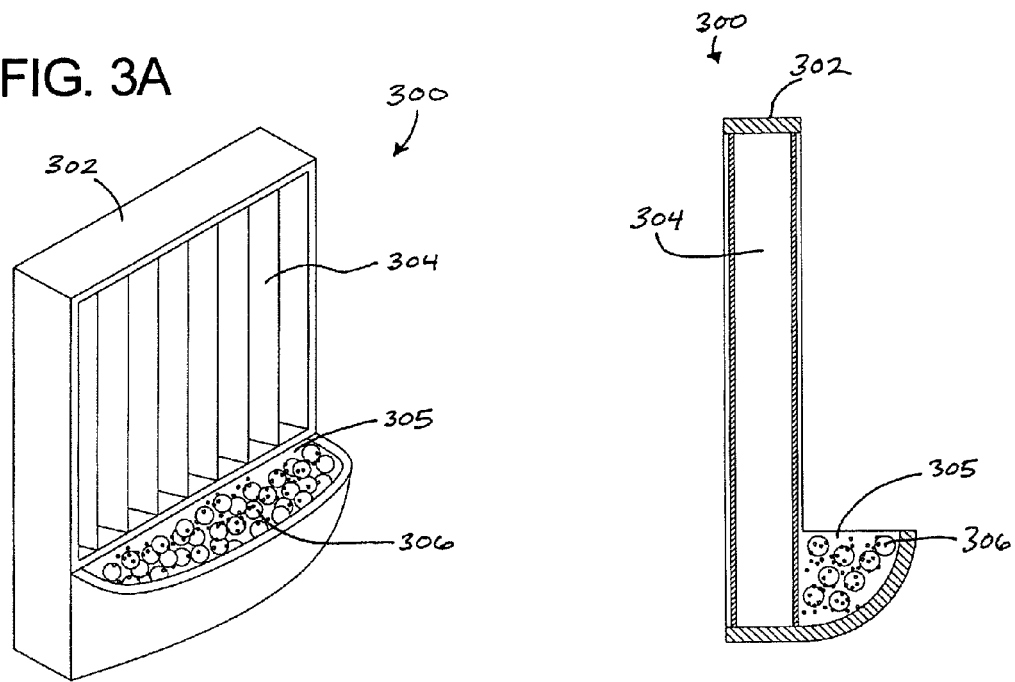
FIG. 3A is a first embodiment of the invention shown for use with a vacuum cleaner filter.
Figure 3B:
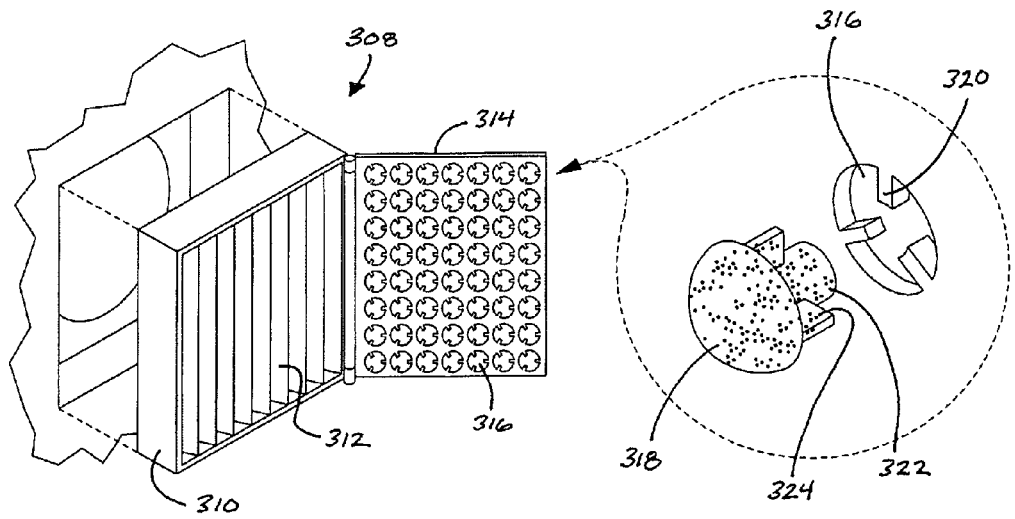
FIG. 3B is a second embodiment of the invention shown for use with a vacuum cleaner filter.
Figure 3C:
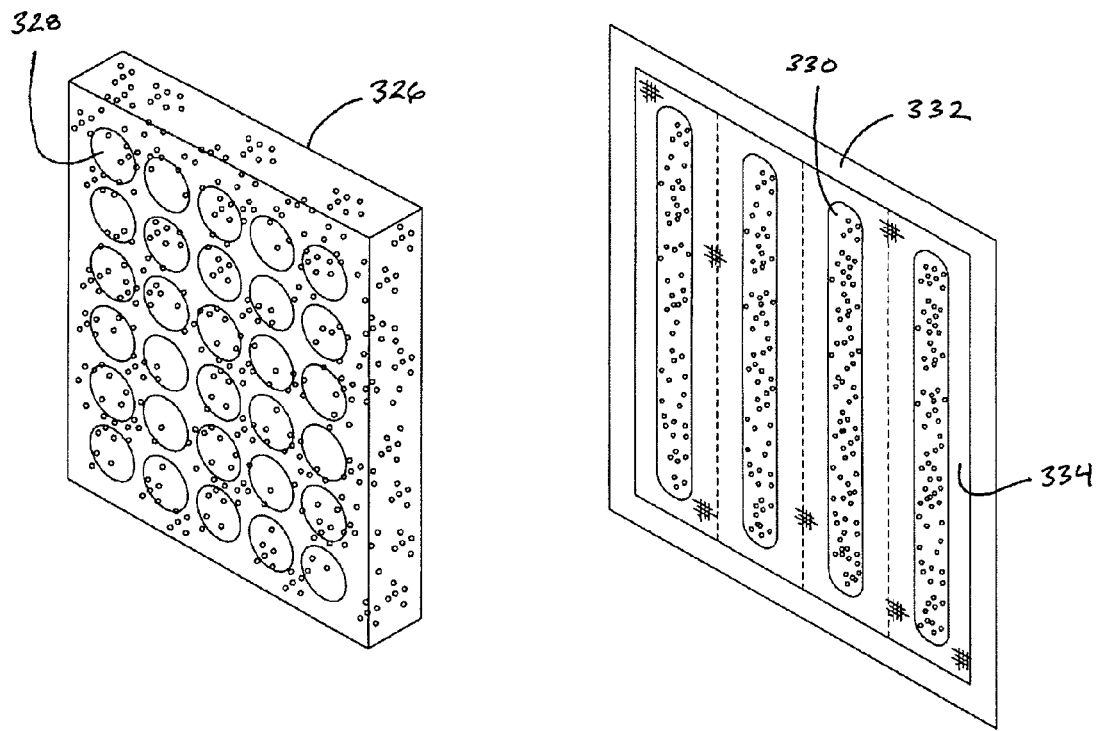
FIG. 3C is a third set of embodiments of the invention shown for use with a vacuum cleaner filter.
Figure 3C:
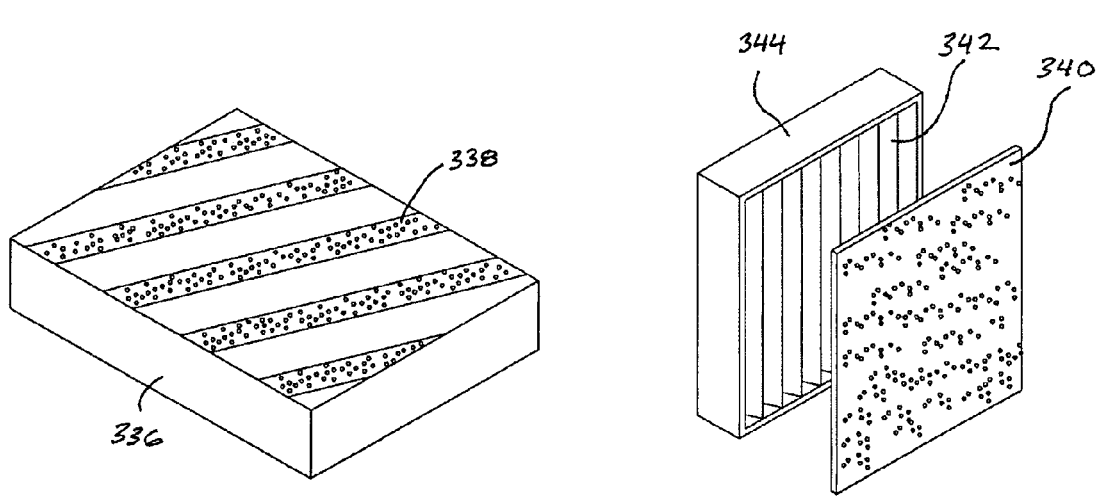

Referring now to FIGS. 3A-3C, the present invention also includes a cleaning device filter having a sodium bicarbonate element or elements integrated into the filter. The sodium bicarbonate is held in proximity to the filter medium, but is located so that it does not unduly inhibit the airflow through the filter medium. The filter may be used as a dirt cup filter, a pre- or post-motor filter, or for any other purpose, and may comprise a pleated filter, planar filter, foam filter, or any other type of airflow filter, and may be made of any material, such as non-woven materials, natural or synthetic fibers, foams, and the like. The filter may have any particle separation efficiency grade, such as HEPA (High Efficiency Particulate Air), ULPA (Ultra Low Penetration, Air), or SULPA (Super Ultra Low Penetration, Air), or may not have a specific filtration grade.

In a first embodiment, shown in FIG. 3A, the present invention provides a filter 300 comprising a frame 302 that holds a pleated or foam filter 304 and has a chamber 305 to hold a supply of solid sodium bicarbonate 306. The frame 302 is arranged such that the air flow passes through the filter medium 304, and at least a portion of the airflow also passes through the chamber 305 so that it is treated by the sodium bicarbonate 306, such as shown in the side cross-sectional view portion of FIG. 3A. The sodium bicarbonate 306 is preferably provided as tablets or spheres that allow a significant amount of airflow therethrough. The chamber 305 can optionally extend across the entire filter medium 304, and may include an air-permeable cover (not shown) to hold the sodium bicarbonate in place. The filter medium 304 may be washable, in which case the user would either remove the sodium bicarbonate before washing the filter medium 304, and replace it afterwards, or put a new supply of sodium bicarbonate in the chamber 305 after each wash.

In another embodiment, shown in FIG. 3B, the invention provides a filter 308 having a generally conventional frame 310 that holds the filter medium 312. The frame 310 also includes a hinged door 314 that can be pivoted to cover the filter medium 312. The door 314 includes a number of openings 316 through which air can pass to the filter medium 312. Some or all of the openings 316 are provided with sodium bicarbonate tablets 318 that fit in the openings 316 without entirely blocking them. This can be accomplished in any number of ways, but is preferably done by providing each opening 316 with a number of flex arms 320 into which a projecting pin 322 on the sodium bicarbonate tablet 318 frictionally fits. Standoff ribs 324 on the tablet 318 prevent the tablet 318 from fitting flush against the door 314 and blocking the openings 316. When the door 314 is closed, the tablets 318 are captured against the filter medium 312. In this embodiment, the tablets 318, door 314, or the entire filter 308 may be replaceable. While the door 314 is shown being pivotable on hinges, it will be appreciated that it may simply comprise a separate part that is placed adjacent the filter medium 312 or snapped in place, or may be fixed in place. In variations of this embodiment, the sodium bicarbonate may alternatively be adapted to clip onto conventional filters by friction fit, which may be accomplished by providing a sodium bicarbonate tablet with a slot that fits over a filter pleat and is held in place by friction and/or gripping teeth formed in the slot. The sodium bicarbonate may also be provide as tablets that have pins or other devices that allow them to be attached to any filter.

In another embodiment, shown in FIG. 3C, a sacrificial perforated sodium bicarbonate plate 326 is provided. The plate 326 has a number of holes 328 to allow air to pass therethrough, and is shaped such that it fits against a conventional filter or elsewhere in the cleaning device's airflow path. The sodium bicarbonate plate 326 may be captured in place when it is installed between the filter, the cleaner housing and the filter cover, or may be provided with snaps or other fasteners to hold it in place. While the holes 328 are shown as being relatively large, the sodium bicarbonate plate 326 may instead be formed with small holes or such that it appears solid but actually has a high air permeability to allow the air to pass through the plate itself.

In another embodiment of FIG. 3C, one or more solid sodium bicarbonate forms 330 or powder sachets are positioned in a frame 332 that is adapted to fit adjacent a conventional filter. The forms 330 are held generally in place on or by a mesh web 334 within the frame 332. Each form 330 may be adhered to the mesh web 334, or they may be captured in place between two meshes. The mesh is preferably large enough that it does not inhibit the airflow to the filter, but may be made of a filter material.

In still another embodiment of FIG. 3C, sodium bicarbonate can be adhered to, painted, or printed on a conventional filter medium 336 of any type. In this embodiment, the sodium bicarbonate is printed on the filter medium 336 in strips 338 or other patterns so that it does not unduly inhibit the airflow through the filter.

In still another embodiment, of FIG. 3C, the sodium bicarbonate is applied to a sheet 340 that located adjacent to a conventional filter 342, such as a pleated or foam filter. A suitable deodorizing sheet 340 and methods for making such a sheet are described in detail herein with reference to FIGS. 10A-12B. In this embodiment, the sheet 340 is preferably adhered to the filter by a pattern of air-impervious adhesive that covers about 5% to about 20% of the sheet's surface area, but other types of attachment may be used. Furthermore, it is also envisioned that the sheet 340 may be captured in place against the filter 342 by being installed within a frame 344 that holds the filter 342, or the sheet 340 may be directly attached to the frame 344. In addition, the sheet 340 may be provided as a separate part that may be placed against the filter 342 when it is installed in a vacuum cleaner. While the sheet 340 is shown having approximately the same planar area as the filter 342, it may be larger or smaller, as needed. In addition, while the filter in FIG. 3C is shown as being flat (or somewhat curved, which would still generally be considered a flat filter), it mat instead be cylindrical, frustoconical, conical, or have any other three-dimensional shape as needed for a particular vacuum application.

Figure 4A:
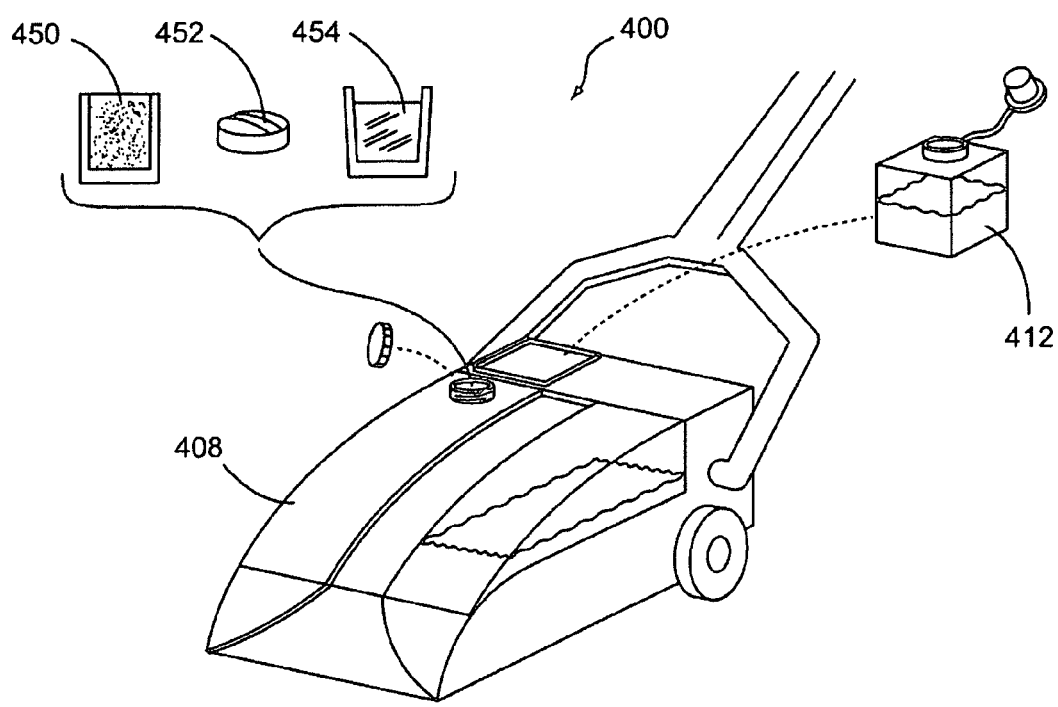
FIG. 4A is an embodiment of the present invention shown in conjunction with an upright wet extractor.
Figure 4B:
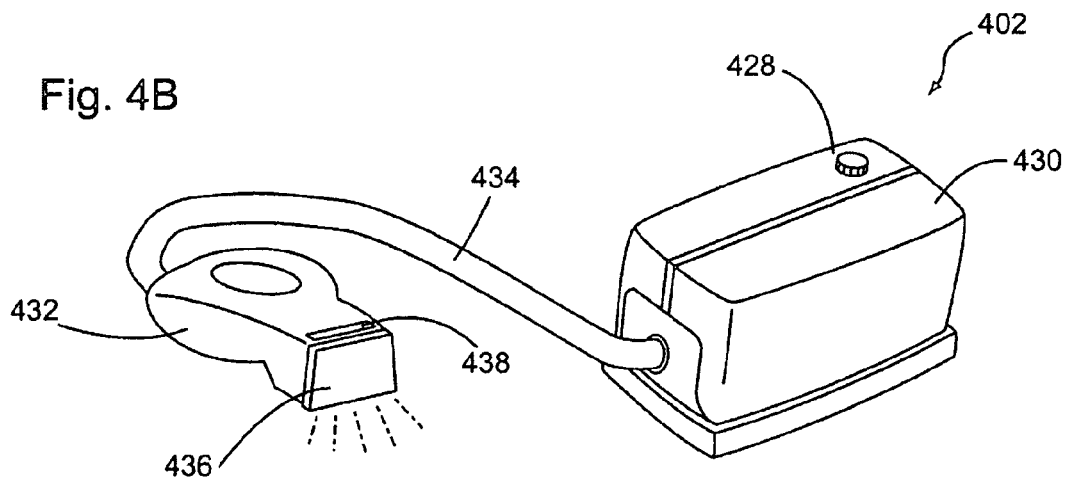
FIG. 4B is an embodiment of the present invention shown in conjunction with a canister wet extractor.

Referring now to FIGS. 4A-4F, the present invention also provides a sodium bicarbonate chemical neutralizer in conjunction with wet extraction cleaning machines. Non-limiting examples of wet extractors and features thereof that may be used with the present invention are shown in U.S. Pat. Nos. 4,910,828 and 5,933,912, which are incorporated herein by reference. FIG. 4A shows an upright wet extractor 400 and FIG. 4B shows a portable canister wet extractor 402 that may be used with the present invention.

The upright wet extractor 400 of FIG. 4A comprises a floor-contacting base 404 to which an upright handle 406 is pivotally attached and used to guide the base 404 on the carpet or other surface to be cleaned. The upright extractor 400 has a supply tank 408 in which a supply of clean water or detergent is contained, and a recovery tank 410 for holding dirt and dirty fluid recovered from the carpet. The extractor 400 may also include a separate auxiliary tank 412 that contains a separate supply of detergent for mixing with the fluid from the supply tank 408. The base 404 also includes one or more sprayers (not shown) or other fluid deposition devices, and an inlet nozzle 414 that is directed downwards to the carpet. A fluid pump or gravity-feed system conveys the cleaning fluid from the supply tank 408 and auxiliary tank 412, if one is used, to the sprayers. A vacuum fan (not shown) is used to generate a working air flow into the inlet nozzle 414 and through the recovery tank 410, as known in the art. The various working parts of the wet extractors 400, 402 are generally known in the art, and shown in U.S. Pat. Nos. 4,910,828 and 5,933,912, and elsewhere.

The portable extractor 402 of FIG. 4B is similar to the upright extractor 400, and has its own supply tank 428, recovery tank 430, suction fan (not shown), and fluid pumping system (not shown). The portable extractor 402 uses a handheld cleaning tool 432, which is attached to the extractor base by a flexible vacuum hose 434. The vacuum hose 434 also includes a fluid supply hose (not shown), which can be external or internal to the hose 434. The cleaning tool 432 has one or more sprayers (not shown) and an inlet nozzle 436 to recover the deposited fluid and dirt entrained therein.

Sodium bicarbonate 403 can be introduced into either wet extractor 400, 402 in a number of ways. In a first embodiment of the invention, the sodium bicarbonate 403 is placed directly in the supply tank 408 in a powder 450, tablet 452, or liquid 454 form, and distributed on the carpet with the cleaning fluid. In another embodiment, the sodium bicarbonate is placed in the separate auxiliary tank 412, and mixed with clean water from the supply tank 408. In this embodiment, the sodium bicarbonate may be used alone as a liquid concentrate, or may be mixed with detergents or other chemicals in the auxiliary tank 412. The mixture ratio of the sodium bicarbonate and the clean water may be fixed or variable, and any type of metering system may be used to control the mixture of sodium bicarbonate concentrate from the auxiliary tank 412 with the clean water from the supply tank 408. Such metering systems are known in the art, and shown, for example, in U.S. Pat. Nos. 4,570,856 and 6,286,180, which are incorporated by reference herein.

Figure 4C:
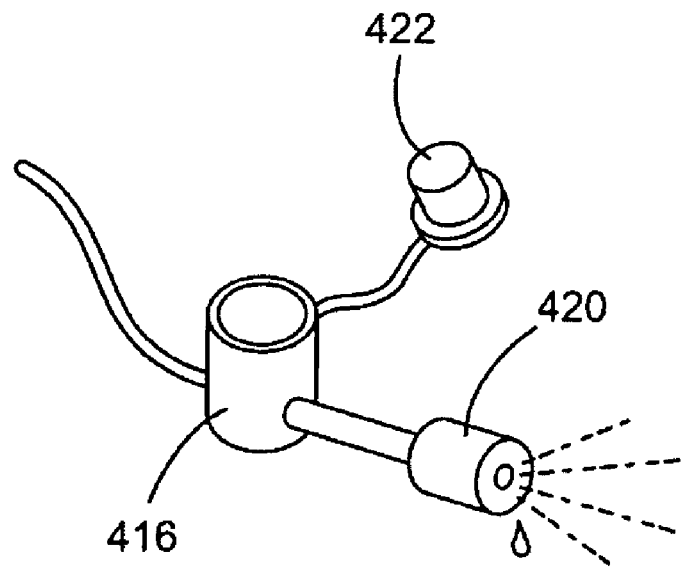
FIG. 4C is an embodiment of a pass-through sodium bicarbonate reservoir of the present invention.

In another embodiment, the sodium bicarbonate is located in one or more pass-through reservoirs located in the fluid flow path between the supply tank 408 and the sprayer(s). For example, FIG. 4C illustrates a sodium bicarbonate reservoir 416 for the upright wet extractor 400 that is located along a fluid hose 418 that leads from the supply tank 408 to a spray nozzle 420. This configuration is also used with the portable extractor 402, in which a pass-through reservoir 438 is located in the cleaning tool 432. Either reservoir 416, 438 may be replaced by a liquid concentrate reservoir that introduces a metered supply of concentrated liquid sodium bicarbonate into the fluid from the supply tank 428, as described above, and such a liquid concentrate reservoir and the shown reservoirs of 416, 438 may be selectively removable from the device.

The pass-through reservoir 416 of FIG. 4C has a removable lid 422 so that it can be refilled when necessary. The lid 422 is preferably readily accessible by the operator, either by being located on the outer surface of the device, or by being accessed upon removal of the supply tank 408 or other removable parts. While the reservoir 416 is shown adjacent the sprayer 420, it may be located elsewhere in the fluid flow path, and may also be formed integrally with the sprayer 420, the supply tank 408, the pump housing (not shown) or other parts of the device. The wet extractor 400, 402 may also include one or more other sprayers that do not have pass-through reservoirs, and a fluid bypass system (such as valves or separate fluid pumps) that allows the user to select which sprayers are used. With this arrangement, the operator can stop and start the use of the sodium bicarbonate by selectively activating the sprayer(s) having the pass-through reservoirs 416 associated therewith.

Figure 4D:
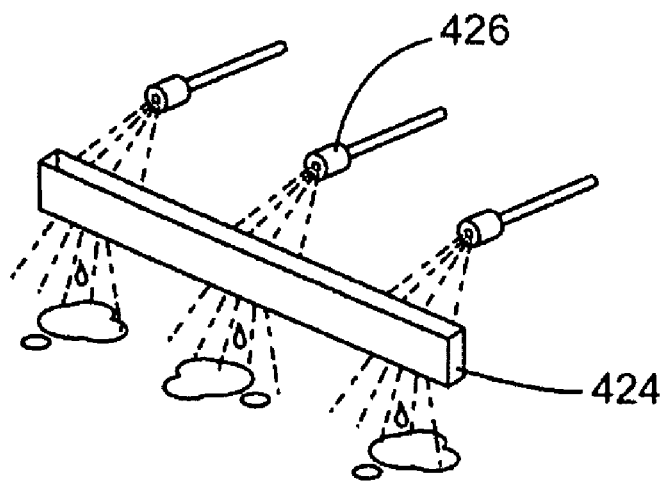
FIG. 4D is an embodiment of a sodium bicarbonate reservoir of the present invention.

In a variation of the foregoing embodiment shown in FIG. 4D, the pass-through reservoir 416 may comprise a reservoir 424 that is located adjacent the exit of the extractor's spray nozzles 426 to receive all or a portion of the sprayed fluid. In this embodiment, the reservoir 424 may comprise a tray into which the sodium bicarbonate is placed to mix with the sprayed or poured fluid. Such a reservoir 424 may also be replaced by a solid bar of sodium bicarbonate that is struck by the emerging spray and slowly eroded and deposited on the surface being cleaned.

In any of the forgoing embodiments in which the sodium bicarbonate is placed in a reservoir, the reservoir may be provided with a filter to prevent large sodium bicarbonate particles from clogging the wet extractor's fluid deposition system.

Figure 4E:
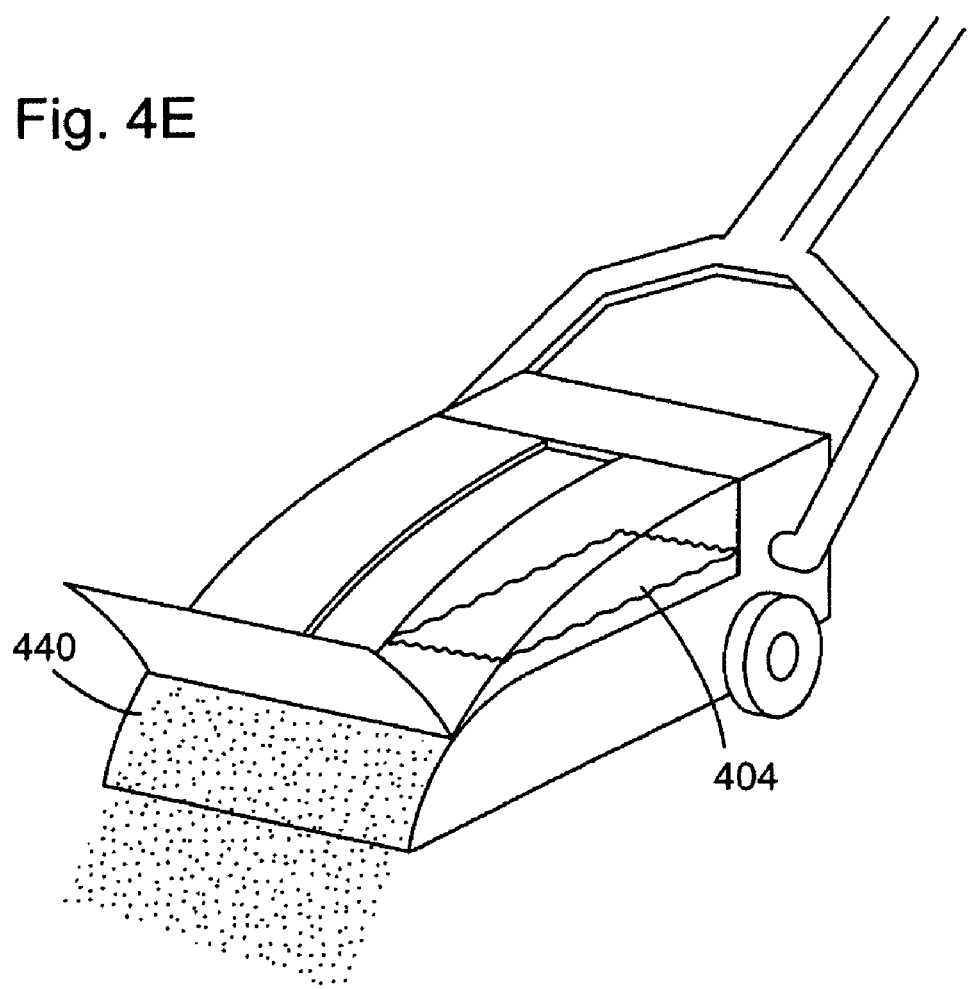
FIG. 4E is an embodiment of the present invention comprising a wet extractor having a dry deposition system associated therewith.
Figure 4F:
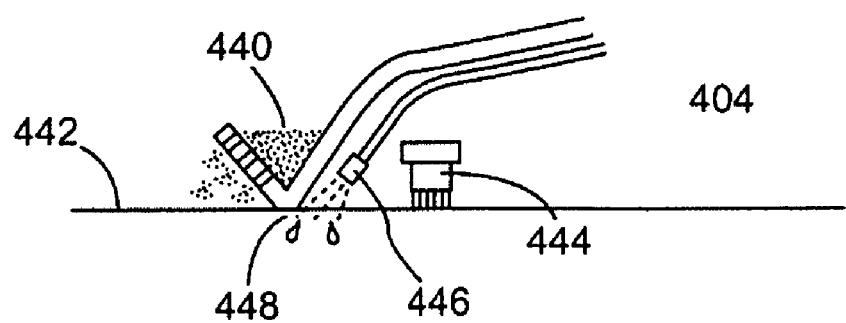
FIG. 4F is a schematic cutaway side view of the embodiment of FIG. 4E.

In another embodiment of the invention shown in FIGS. 4E and 4F, the sodium bicarbonate is provided in a powder form that is deposited on the surface being cleaned, rather than being supplied with the cleaning fluid. In this embodiment, the extractor base 404 (or cleaning tool 432) includes a sodium bicarbonate receptacle 440 located on the front of the base 404. The receptacle 440 has a manually or automatically controlled deposition slot that opens to allow sodium bicarbonate to fall onto the surface being cleaned. Such powder deposition systems are known in the art. The powdered sodium bicarbonate is then worked into the surface 442 by an agitator brush 444, which can help loosen dirt and debris and gently abrade the surface being cleaned. Fluid may be simultaneously or subsequently deposited on the surface 442 by one or more sprayers 446, and the fluid, dirt, and sodium bicarbonate are removed by the suction inlet nozzle 448.

The foregoing examples are not intended to limit the invention, and other variations on using sodium bicarbonate with wet extractors will be appreciated in light of the present disclosure and with practice of the invention. The use of sodium bicarbonate with extractors in the manners described above is expected to provide numerous benefits. For example, it is expected to provide additional cleaning benefits by virtue of the mildly abrasive nature of the sodium bicarbonate. It is also expected to enhance odor neutralization in the surface being cleaned by leaving a slight residue of sodium bicarbonate thereon. The recovered sodium bicarbonate is also expected to reduce odors in the supply tanks, as well as in the inlet nozzle 414, 436, vacuum hose 434, and recovery tank 410, 430. This can be particularly advantageous when the extractor is used frequently, or is used infrequently and not thoroughly cleaned after every use. The sodium bicarbonate should also reduce odors in the sink or other receptacle into which the recovery tank may be emptied.

Figure 5A:
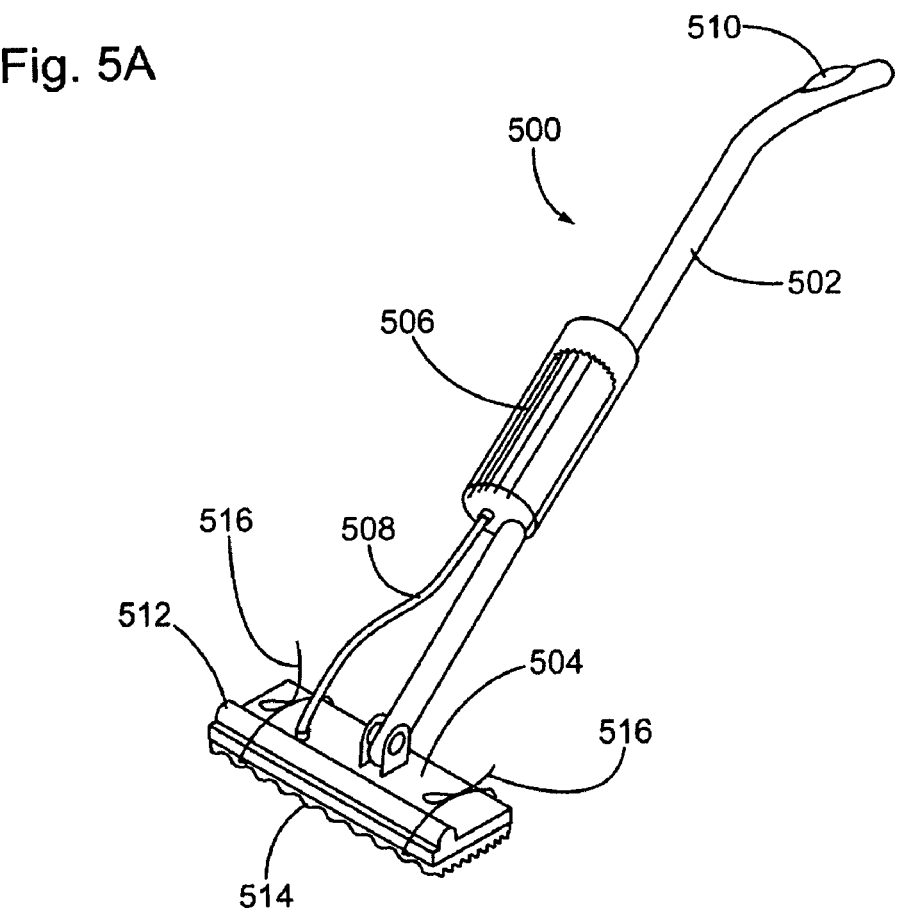
FIG. 5A is an embodiment of the present invention shown in conjunction with a cleaning wand.
Figure 5A:
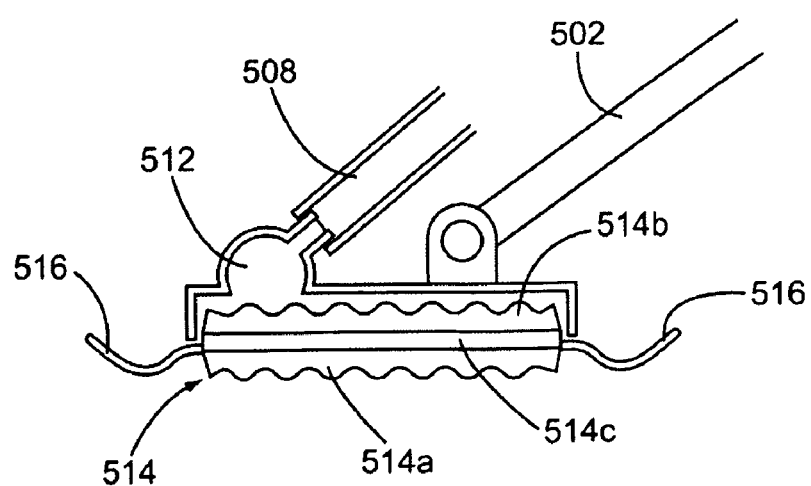
Figure 5B:
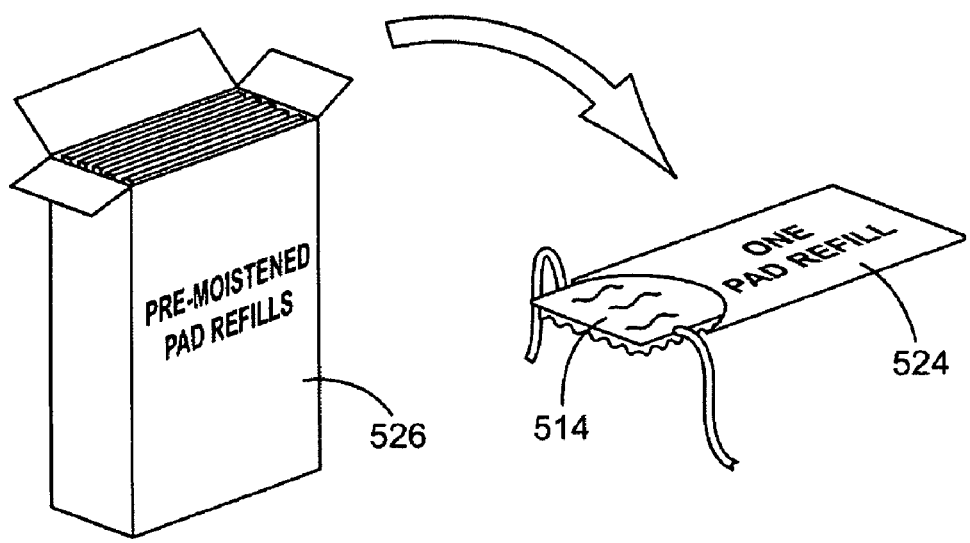
FIG. 5B is two embodiments of sodium bicarbonate cleaning pads that may be used with the embodiment of FIG. 5A.
Figure 5B:
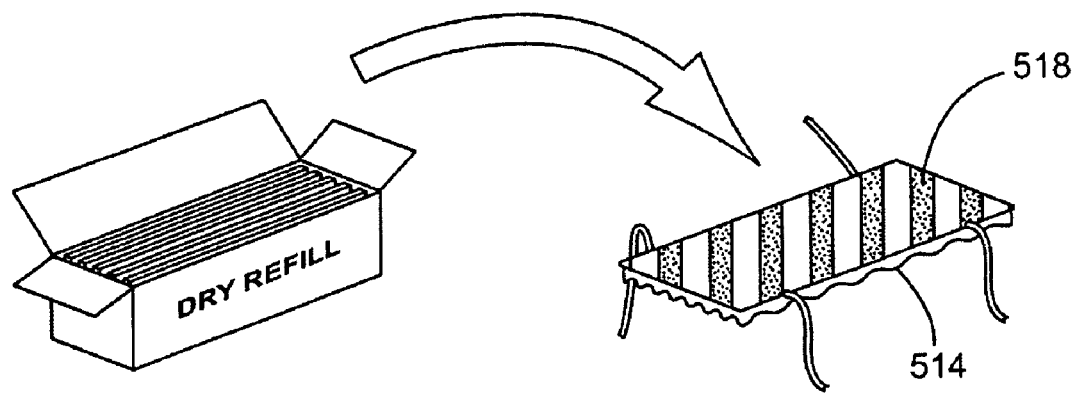
Figure 5C:
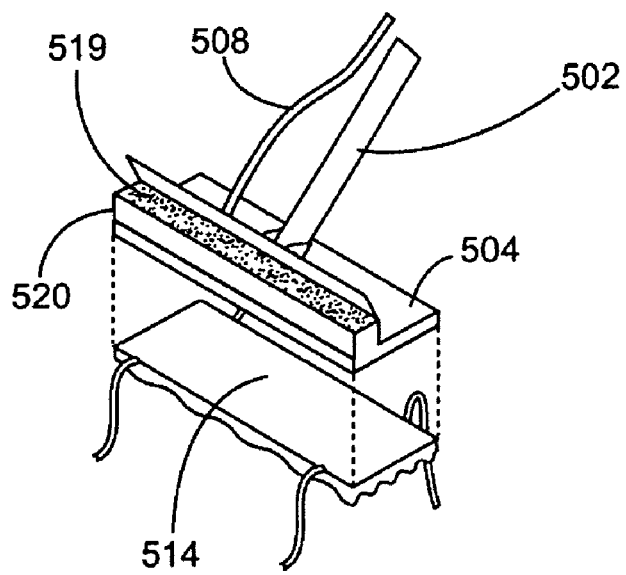
FIG. 5C illustrates alternative variations of the embodiment of FIG. 5A.
Figure 5C:
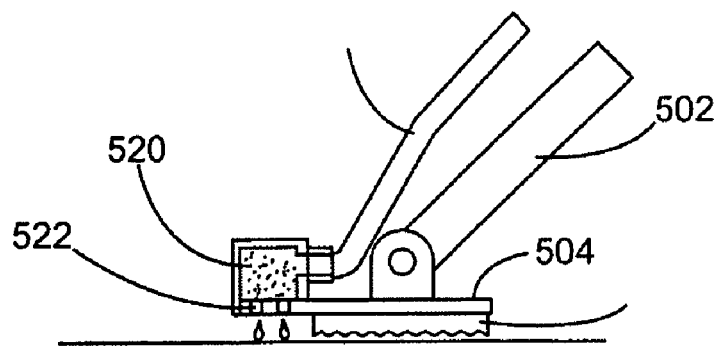
Figure 5C:
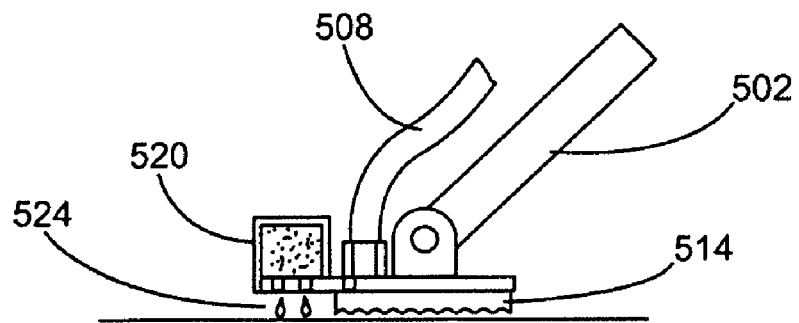

Referring now to FIGS. 5A-5C, the present invention also provides a sodium bicarbonate chemical neutralizer in conjunction with a floor cleaning wand 500. The cleaning wand 500 comprises a handle 502 having a cleaning head 504 pivotally attached thereto. Such cleaning wands are known in the art, and typically used in conjunction with a disposable dry or pre-moistened cleaning pad that fits on the bottom of the cleaning head 504.

In a first variation of the present invention, shown in FIG. 5A, the cleaning wand 500 has a fluid reservoir 506 that is attached to the cleaning head 504 by a hose 508. A suitable control valve (not shown) is provided so that an operator can stop or control the fluid flow from the reservoir 506 to the head 504, preferably by a controller 510 located in the grip portion of the handle 502. The hose 508 enters a manifold 512 on the cleaning head 504, which distributes the fluid across the width of the cleaning head 504.

In this embodiment, the device is provided with a cleaning pad 514, which is retained on the cleaning head 504 by any suitable device, such as strings 516, clips or other devices. The cleaning pad 514 has a multilayered construction having a first layer 514a, a second layer 514b, and a third layer 514c sandwiched between the first and second layers. The first and second layers 514a, 514b preferably comprise fabric, sponge or non-woven materials. The third layer preferably comprises a layer of sodium bicarbonate in solid or powder form.

The cleaning pad 514 may be provided in any suitable form. For example, as shown in FIG. 5B, the pad 514 may be provided as a pre-moistened pad that is impregnated with a sodium bicarbonate liquid. In this embodiment, each pad 514 can be conveniently packages individually in sealed pouches 524, which are collected in a box 526. The pads 514 may also be provided in a dry form having sodium bicarbonate printed or painted thereon in strips 518, or in other patterns. When the cleaning pad 514 is of the pre-moistened type, it may not be necessary to use the fluid reservoir 506. During use, the fluid from the pad 514 and/or reservoir 506 moistens the cleaning pad 514 and releases the sodium bicarbonate onto the surface being cleaned, where it helps chemically neutralize offensive odors, and may serve as a mild abrasive to help polish the surface.

In a variation of this embodiment, shown in FIG. 5C, the sodium bicarbonate 519 is contained in a tray 520 on the cleaning head 504 in a solid or powdered form. The fluid hose 508 enters the tray 520 and fluid from the reservoir 506 saturates the sodium bicarbonate and releases it onto the surface being cleaned through holes 522 on the bottom of the cleaning head 504. In a further variation of this embodiment, the fluid hose 508 is instead attached to deposit fluid onto the floor or into the cleaning pad 514, and the sodium bicarbonate is deposited in a powder form 524. In still another variation of the invention (not shown), the sodium bicarbonate may be provided as a liquid mixture that is contained in the reservoir 506, and deposited into the cleaning pad 514 or directly on the floor when desired.

Figure 6:
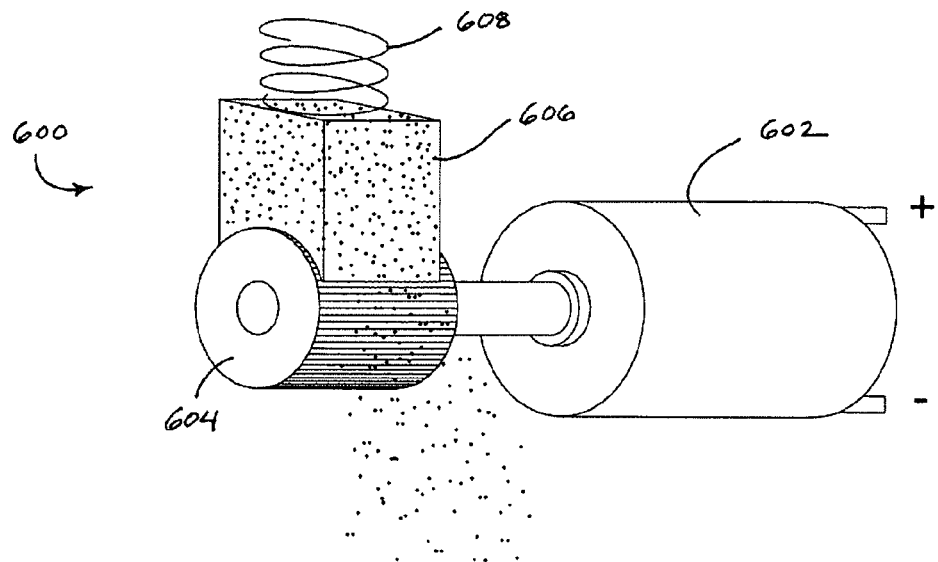
FIG. 6 is an embodiment of a sodium bicarbonate deposition system of the present invention.

It is also envisioned that the sodium bicarbonate can be provided in a solid form and ground into a powder when odor removal is desired. Variations on this embodiment are shown in FIGS. 6 and 7A-7G. These deposition systems may be used in conjunction with any type of vacuum cleaner, central vacuum system, extractor, or cleaning wand. A first of these embodiments is shown in FIG. 6. In this embodiment, the sodium bicarbonate deposition system 600 comprises an electric motor 602 or air-turbine drive that rotates an abrasive drum 604. A solid sodium bicarbonate block 606 is located adjacent the abrasive drum 604, and biased against it by a spring 608. When the drum 604 rotates, it abrades the block 606 and deposits powdered or fragmented sodium bicarbonate on the surface being treated, onto a cleaning pad, into a fluid reservoir for mixture with fluid therein, or into a dustcup or dustbag interior. This deposition system 600 can be controlled either by selectively operating the motor 602, or by selectively contacting the sodium bicarbonate block 606 against the abrasive drum 604. The degree of sodium bicarbonate deposition can be controlled by altering the speed of the drum 604 or the pressure or speed at which the block 606 is fed into the drum 604, or the surface area of the block 606 contacting the drum 604. Of course, in other embodiments, the drum 604 may be replaced by other abrading devices, such as a rotating disk, a reciprocating file, and so on. In still other embodiments, the drum 604 or other abrading device may be turned manually by the vacuum operator, via a hand-crank, turning knob, or other suitable mechanism.

Figure 7A:
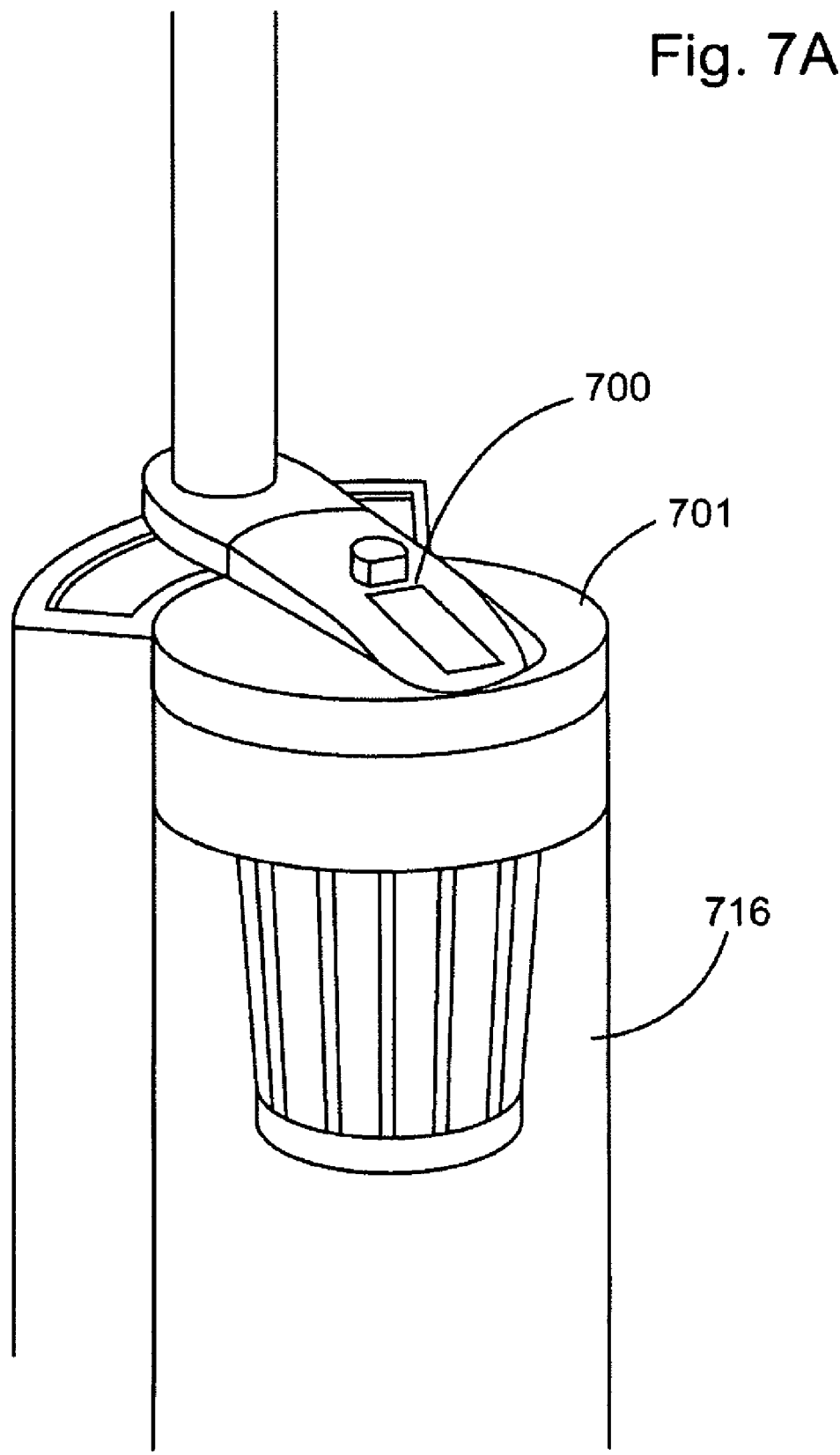
FIG. 7A is an embodiment of a sodium bicarbonate deposition system of the present invention as attached to a cyclonic-type dustcup.

Referring now to FIGS. 7A-7G, another embodiment of a deposition system 700 comprises a solid sodium bicarbonate bar or rod 702 that can be ground manually by the vacuum operator. While the deposition system 700 may be located anywhere where the sodium bicarbonate particles 708 can mingle with the dirt captured by the vacuum cleaner, in a preferred embodiment, it is attached to a dustcup lid 701, as shown in FIG. 7A, to enable the sodium bicarbonate particles 708 to be deposited directly into a dustcup interior. In this embodiment, the deposition system 700 is located generally at the top of the dustcup lid 701, which in turn is mounted to the top of a dustcup 716 of a conventional cyclonic or dustcup vacuum cleaner. Here, the deposition system 700 is easily accessed by a user.

Figure 7B:
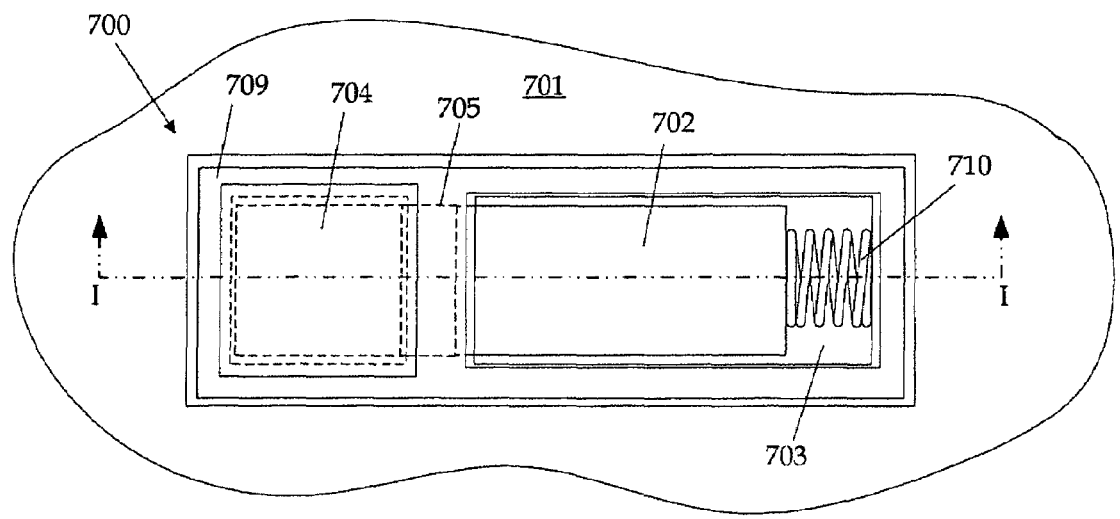
FIG. 7B is top, plan view of the embodiment depicted in FIG. 7A.
Figure 7C:
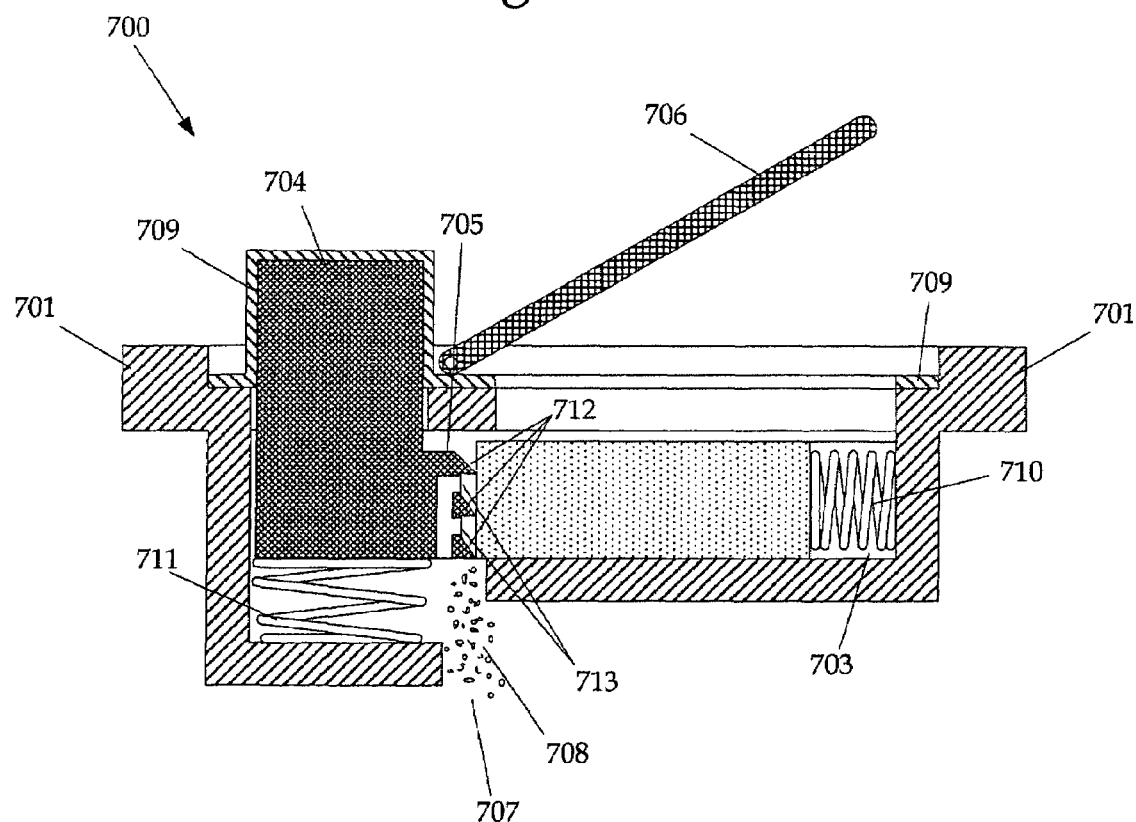
FIG. 7C is a cross-sectional view of the embodiment depicted in FIG. 7B, shown along line I-I thereof.

Referring to FIGS. 7B and 7C, a pocket or recessed area 703 is provided in a dustcup lid 701. The pocket 703 is constructed of a size and geometry to at least partially accept and hold the sodium bicarbonate bar 702. The pocket 703 is in communication with the dustcup interior by one or more holes 707 to allow abraded particles 708 to easily drop into the dustcup interior. A spring 710 is provided within the pocket 703, and opposite the abrasion surface 705, to bias the bar 702 against an abrasion surface 705, which is mounted on a movable plunger 704. A pocket cover 706 is also provided to retain the bar 702 within the pocket 703. The pocket cover 706 is preferably pivotally attached to the dustcup lid 701 as shown in FIG. 7C. (The pocket cover 706 is not shown in FIGS. 7B, 7D, or 7F, to preserve the clarity of those Figures.) Alternatively, the cover 706 may be completely removable or omitted. The pocket cover 706 may be secured to the dustcup lid 701 and pocket 703 by a latch, snap, friction fitting, or other attachment devices as generally known in the art.

The plunger 704 and abrasion surface 705 are provided on the dustcup lid 701 and positioned such that the plunger 704 slides the abrasion surface 705 relative to the sodium bicarbonate bar 702. This relative movement abrades the bar 702 and creates sodium bicarbonate particles 708, which fall through a hole 707 into the dustcup. The plunger 704 and abrasion surface 705 may be formed integrally as a single part, or may alternatively be manufactured as two separate and assembled or operatively associated pieces. The plunger 704 is also preferably biased by a spring 711 in an up position requiring the operator to only push the plunger 704 to grind the bar 702. This arrangement allows the user to press and release the plunger 704 repeatedly until the desired amount of sodium bicarbonate particles 708 is generated.

Alternatively, the plunger 704 may instead be biased in a down position or not biased at all. If the plunger 704 is not biased in either direction, the user will have to both push and pull on the plunger 704 to generate the particles 708. If the plunger 704 is only biased in a down position, then the user will only need to pull and release the plunger 704. Requiring a user to pull on the plunger 704 will likely require a pull handle on the plunger 704. For simplicity, such a handle is not depicted.

Other variations of the plunger-style deposition system 700 may include a side moving plunger 704, an electrically powered plunger 704, or a combination of both. Examples of electrically powered plungers may include coupling the plunger 704 to a solenoid, linear motor, or an electric motor or air-turbine drive coupled to the plunger 704 via a cam, crankshaft and piston combination, or other mechanical arrangement to create the linear motion. Such electric and mechanical devices are generally known in the art and are therefore not shown.

The abrasion surface 705 should be manufactured from a material hard and tough enough to successfully abrade the sodium bicarbonate bar 702 and not break apart itself. Most hard plastics, such as structural ABS plastic, should be suitable. The abrasion surface teeth 712 should be spaced sufficiently apart to reduce the likelihood of sodium bicarbonate powder and dust accumulating on the abrasion surface 705 and reducing the abrasion surface's effectiveness. In addition, the abrasion surface 705 may be provided with teeth 712 that cut on the pushing stroke, the return stroke, or both.

Other variations on the abrasion surface 705 provide openings 713 in the abrasion surface 705 between the teeth 712. These openings 713 allow freshly abraded sodium bicarbonate particles 708 to pass from the sodium bicarbonate bar 702 and through the abrasion surface 705 to reach the dustcup interior. Any powder accumulating between the teeth 712 would be pushed through these openings 713 at the abrasion surface's 705 next passing over the sodium bicarbonate bar 702. Thus, openings 713 in the abrasion surface 705 act to reduce the likelihood of sodium bicarbonate powder sticking between the abrasion surface teeth 712 and reducing the abrasion surface's 705 effectiveness.

Another element of deposition system 700 of FIGS. 7B and 7C is a gasket 709 that seals the dustcup lid 701 at the deposition system 700. The gasket 709 comprises a resilient membrane that covers the plunger 704, with the plunger 704 being on the dustcup interior side of the gasket membrane. The gasket 709 passes between the lid 701 and the pocket cover 706 to allow access to the cover 706. The gasket 709 may be molded or machined in to the desired shape prior to attachment to the lid 701, or may be thermoformed to the proper shape after attachment. The gasket 709 is preferably made of a resilient elastomeric compound such as, neoprene; isobutene-isoprene, commonly known as butyl; ethylene propylene diene monomer, commonly known as EPDM; hydrogenated nitrile butadiene rubber, commonly known as HNBR; or HYPALON® sold by Dupont Performance Elastomers of Wilmington, Del. Any suitable means may be used to attach the gasket 709 to either the dustcup lid 701 or the pocket cover 706. For example, the gasket may be attached by an adhesive, ultrasonic welding, heat sealing, laser welding, chemical bonding, or, if the lid 701 or cover 706 are plastic, molded in place during an injection molding process. Such methods are generally known in the art.

As shown in FIG. 7C, the gasket 709 seals the lid 701 by passing over the plunger 704, and beneath the pocket cover 706. Alternatively, the gasket 709 may be provided only around the plunger 704, only around the pocket cover 706, or omitted entirely. When used, the gasket 709 helps prevent dust or debris from spilling from the dustcup during vacuum idle time, and also ensures that no sodium bicarbonate powder will leak out while the cover 706 is closed. The sealing gasket 709 also reduces air leakage through the deposition system 700 to thereby decrease suction loss at the inlet nozzle.

The embodiment of FIGS. 7B and 7C is expected to be particularly useful where the deposition system 700 is positioned above the location where it is desired to mix the sodium bicarbonate with the dirt, as gravity can easily convey the particles 708 to the desired location. However, in this arrangement, sodium bicarbonate particles 708 may accumulate in the bottom of the pocket 703 and spill out when the operator opens the cover 706 to insert a new bar 702. Sodium bicarbonate particles 708 may also accumulate on the abrasion surface 705 and reduce its effectiveness in abrading the bar 702. To address these potential problems, other variations of the invention provide vacuum assistance in delivering the sodium bicarbonate particles 708 to the dustcup interior (or other final destination). These embodiments do not have a gasket, or purposefully leave an opening in or around the gasket 709, pocket cover 706, or plunger 704 to allow the vacuum to generate an incoming flow of air to convey the particles 708 into the vacuum. It will be appreciated that the use of a controlled incoming airstream may also allow the deposition system 700 to be used where gravity cannot be relied upon to convey the sodium bicarbonate particles 708 to the dirt.

Figure 7D:
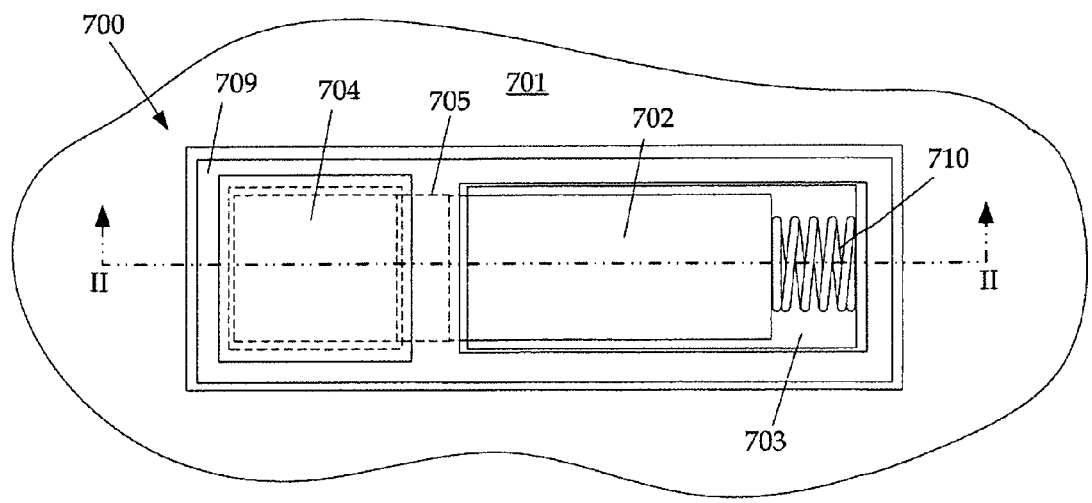
FIG. 7D is top, plan view of one embodiment of a sodium bicarbonate deposition system.
Figure 7E:
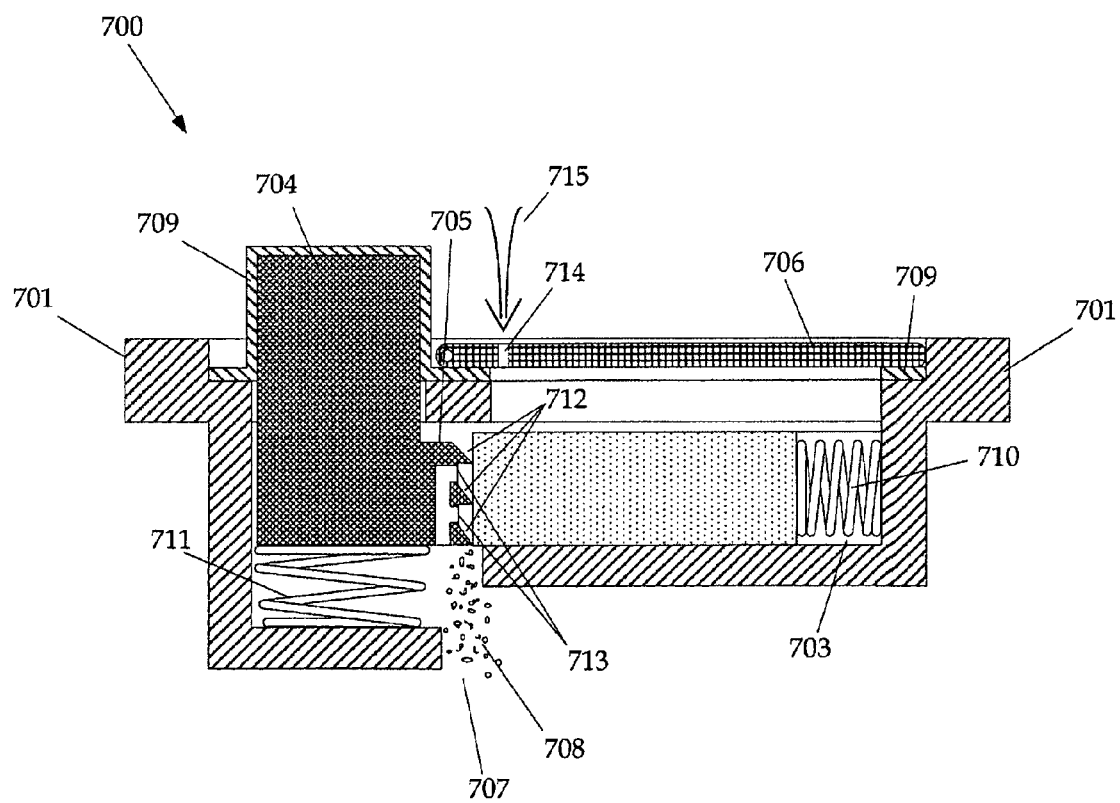
FIG. 7E is a cross-sectional view of the embodiment depicted in FIG. 7D, shown along line II-II thereof.

A first example of the foregoing variations of the invention is shown in FIGS. 7C-7D. In this embodiment, the deposition system 700 is generally the same as the embodiment of FIGS. 7B-7C, and has a sealing gasket 709. However, this embodiment includes an opening 714 in the cover 706 that allows airflow to enter the pocket 703 and clean out any lingering sodium bicarbonate particles 708. The use of such an opening 714 potentially gives manufacturers and designers more control over where and how the airstream 715 enters and moves through the pocket 703. In the shown embodiment, the opening 714 passes through the cover 706 just above the abrasion surface 705 to maximize the airflow at this point. Another embodiment provides the cover 706 with an internal duct taking a tortuous path to the pocket 703 to help reduce the likelihood of any substantial amount of dust or sodium bicarbonate particles 708 escaping from the dustcup during vacuum idle time.

Figure 7F:
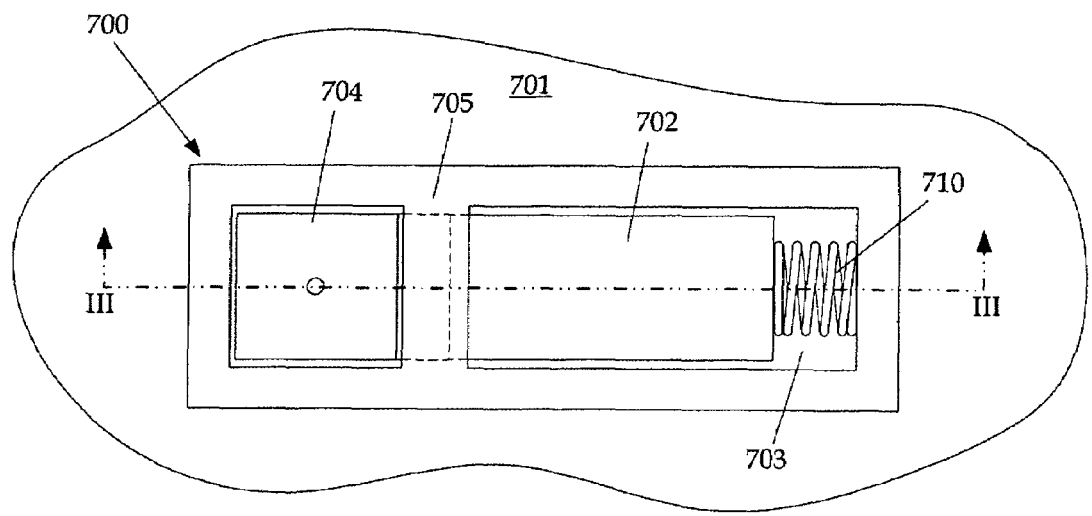
FIG. 7F illustrates another embodiment of a sodium bicarbonate deposition system.
Figure 7G:
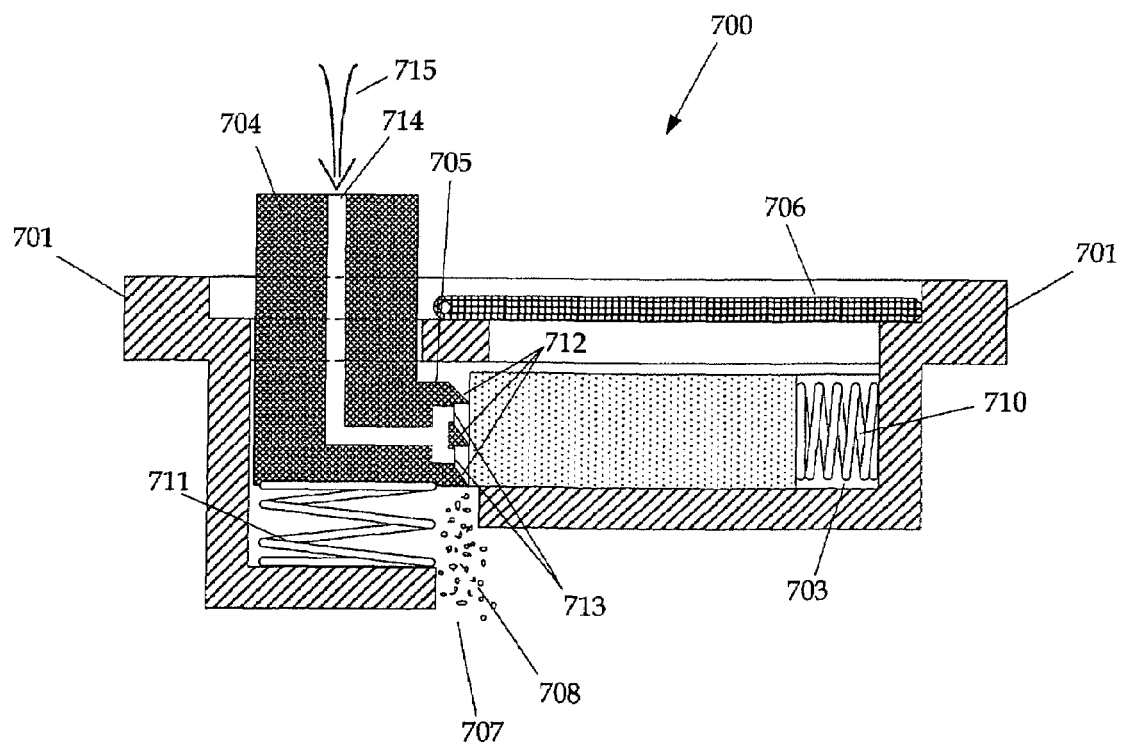
FIG. 7G is a cross-sectional view of the embodiment depicted in FIG. 7F, shown along line III-III thereof.

Referring to FIGS. 7F-7G, another embodiment of the invention comprises an opening 714 formed in the plunger 704, which directs the airstream 715 through the abrasion surface 705. This embodiment helps deliver the particles 708, and helps prevent sodium bicarbonate particles 708 from accumulating between the teeth 712 on the abrasion surface 705. Still other variations on a deposition system 700 having a controlled air entry will be appreciated by those of ordinary skill in the art in view of the present discussion.

The manual deposition system 700 of FIGS. 7A-7G may be placed on a dustcup sidewall, above or adjacent to a dustbag inlet, or on any vacuum cleaner duct or conduit. As noted before, the use of a controlled air entry path may also allow the system 700 to be used in locations where gravity is not available to draw the particles 708 into the vacuum. This air assist can also be increased by locating the hole 707 in the pocket 703 adjacent a relatively low pressure part of the vacuum path, such as adjacent a hose, or at a venturi located in a hose. The system may also be placed on a floor nozzle and be foot actuated, where the particles 708 can be deposited directly on the carpet or surface being vacuumed or directly into the vacuum airstream. The amount of sodium bicarbonate deposited can be controlled by altering the stiffness of the biasing spring 710, the number, pattern, and orientation of the teeth 712 on the abrasion surface 705 and by other modifications, as will be appreciated by those of ordinary skill in the art.

Figure 8:
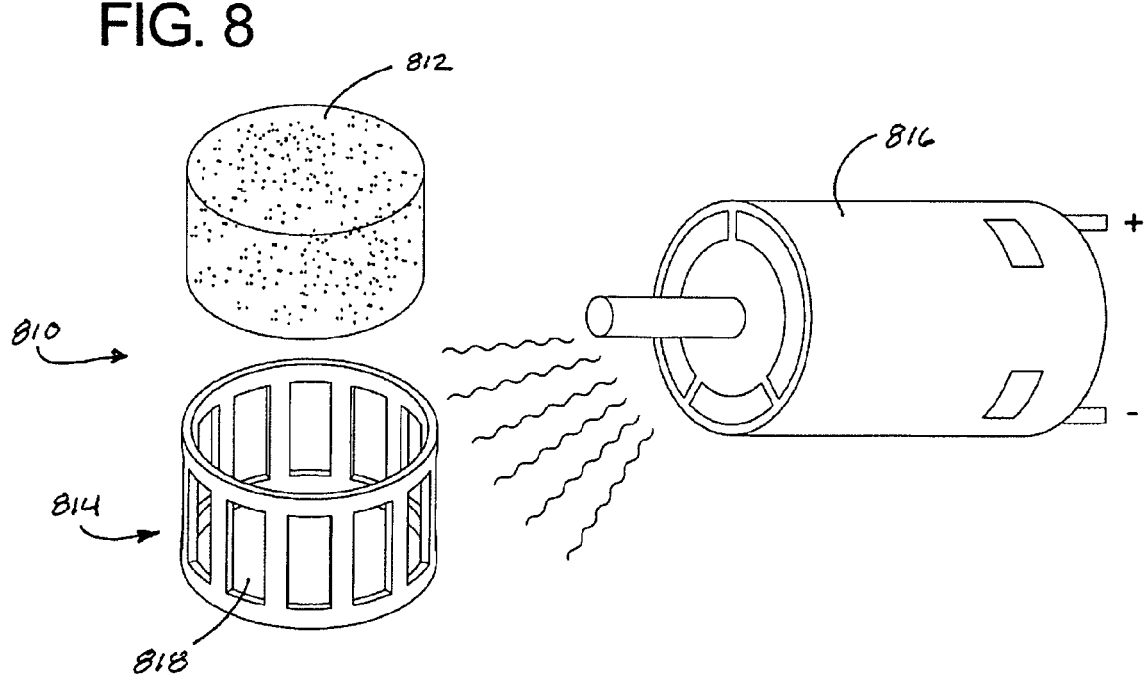
FIG. 8 is an embodiment of a temperature sensitive sodium bicarbonate deposition system of the present invention.

The present invention also contemplates using heat to provide controlled deposition of sodium bicarbonate into the vacuum cleaner. In a further embodiment of a deposition system 810, shown in FIG. 8, the sodium bicarbonate is provided as a powder that is held together in a temperature-sensitive matrix to form a solid block 812. The block 812 is located in a cage 814 or other perforated chamber, and selectively heated to cause the matrix to soften or evaporate. The cage 814 is provided with vents 818 that are sufficient to allow airflow to pass through the cage 814 and to the sodium bicarbonate block 812 and may be made of a thermally conductive material to heat the block 812 by conduction. As the matrix erodes, the sodium bicarbonate is released through the cage vents 818 and onto the surface to be cleaned or into a fluid reservoir (if used in an extractor). A separate heater may be provided to heat the sodium bicarbonate block 812, or heat may be provided from a vacuum motor 816 or other heat source already present in the device.

An additional variation on this embodiment provides airflow vanes (not shown) on the cage vents 818, and means to rotate the cage 814 during vacuum operation. As the cage 814 rotates, the vanes draw air into the cage 814 and to the sodium bicarbonate block 812. The cage 814 may be rotated by the vacuum motor 816, or by a vacuum airflow driven air-turbine drive or other motor, or the vanes may be moved by an incoming airflow (such as the fan motor exhaust). In addition, the sodium bicarbonate block 812 may be secured to the rotating cage 814, or may be stationary relative to the rotating cage 814. The vanes may also act as additional heat sinks to help heat the block 812 by conduction.

Figure 9A:
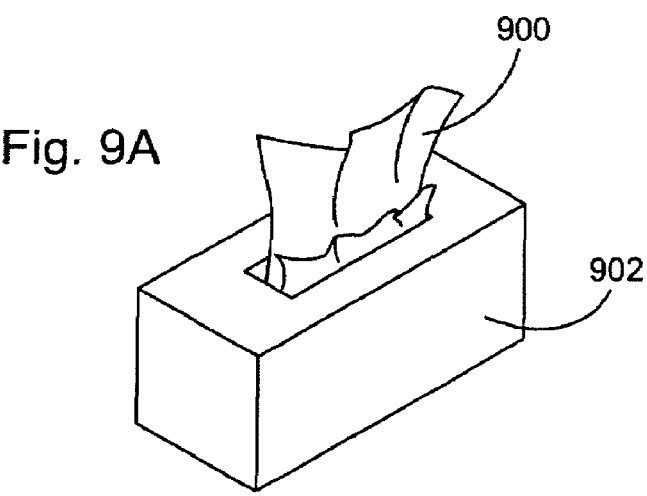
FIG. 9A illustrates an embodiment of a chemically-impregnated deodorizing sheet of the present invention and an accompanying container.
Figure 9B:
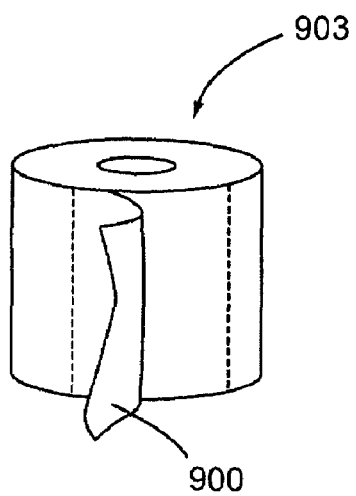
FIG. 9B illustrates an embodiment of a chemically-impregnated deodorizing sheet of the present invention and another form of packaging.
Figure 9C:
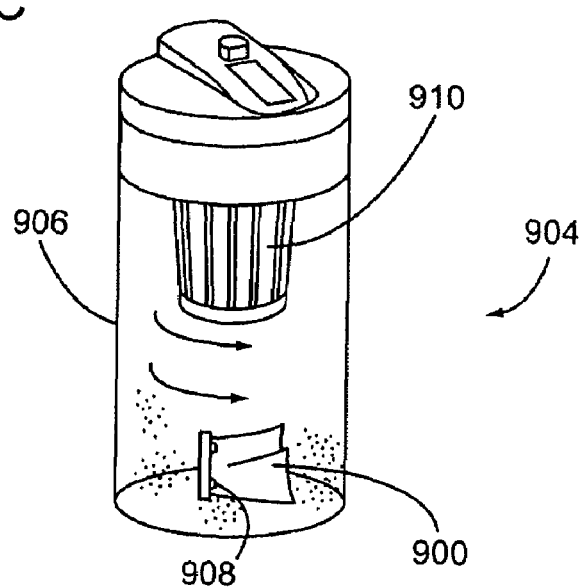
FIG. 9C is an embodiment of a chemically-impregnated deodorizing sheet of the present invention as used in a cyclonic dustcup container.

In another embodiment, shown in FIGS. 9A-9C, the present invention provides a chemically-impregnated loose sheet 900 that can be inserted into a vacuum cleaner dirt bag or other vacuum cleaner dirt container. The sheet 900 comprises a fabric or other material that is impregnated, coated, or otherwise provided with odor-reducing materials, perfumes or other compositions that are useful for killing bacteria, reducing odors, creating pleasant odors, or otherwise making the operation of the vacuum cleaner more pleasant or sanitary. In a preferred embodiment, the sheet 900 is impregnated with sodium bicarbonate, but other materials may be used. The sheet 900 preferably comprises a woven or non-woven fabric material, which may be air permeable or not. The fabric may also comprise a uniform material, or a composite of multiple types and/or layers of material. In a preferred embodiment, the fabric comprises a web of non-woven polyester fibers that are arranged in a random, non-directional manner, and needles to increase the size of the void areas between the fibers to provide additional loft. The fibers may have a coarse or fine denier, and may have a combination of deniers. A suitable material is TYVEK™, which is distributed by E.I. du pont de Nemours and Co. of Richmond, Va. Other suitable materials include non-woven polyester fabrics such as PN232 and PC858 manufactured by the Precision Custom Coatings Company of Totowa, N.J. Of course, any other suitable material, such as a cotton weave, a non-woven polymer, or others, may be used.

Referring to FIGS. 9A and 9B, a sheet 900 of this embodiment of the invention may be inserted into any conventional vacuum cleaner dirt container to help reduce odors and provide other benefits to the cleaning device operation. To this end, the sheet 900 may be provided in a package 902 with multiple sheets 900 therein, and directions for inserting the sheets 900 into the cleaning device for which its use is intended. Such a package 902 may be adapted to be held in the cleaning device itself, such as by being located in a pocket or slot in a vacuum cleaner housing. The cleaning device itself may also be modified to hold sheets 900 when they are not in use. The sheet 900 may alternatively be provided as a perforated roll 903 of material that may be torn to form individual sheets 900 or sachets filled with active material, or in any other suitable form.

When used with conventional dust bag filters, the sheet 900 may be simply inserted into the bag inlet before it is attached to the vacuum cleaner. When used with dirt cup filters, such as the cyclone separator 904 shown in FIG. 9C, the sheet 900 may be attached to the dirt cup 906 by one or more clips 908, or other mechanical or adhesive bonds, to prevent it from wrapping around or otherwise obstructing the cyclone outlet or filter 910. In this embodiment, the sheet 900 may be held tightly in place, or allowed to move into and with the airflow (as shown) to interact with the dirt contained in the dirt cup 906. The shown location of the sheet 900 at the bottom of the cup 906 is preferable to allow the sheet 900 to react with the dirt when the vacuum cleaner is not in use, but this is not required.

Referring now to FIGS. 10A-10H, in a preferred embodiment of the invention, a deodorizing sheet 1000 is provided pre-installed and permanently or removably attached to a bag filter 1012. Preferably, the deodorizing sheet 1000 comprises at least one sheet layer having sodium bicarbonate (and/or other deodorizing compounds) operatively associated with it. Such operative association may be by capturing the sodium bicarbonate within the fibers of the sheet or between multiple sheet layers, adhering the sodium bicarbonate to the sheet material, or by any other technique that generally applies the sodium bicarbonate to the sheet. While firm attachment of the sodium bicarbonate to the sheet may be provided, it may also be desirable to allow the sodium bicarbonate to release from the sheet, at least to some degree, during installation and/or operation. Such release is referred to as "dusting." Furthermore, while particular embodiments of sheet material are described herein, the term "sheet" is understood herein to describe any generally flat material, which may be flexible or not.

A typical bag filter comprises one or more air pervious flexible sheets of material that are assembled together to form a generally air-permeable enclosure. The exemplary bag filters 1012 shown herein comprise sidewalls 1013, one or more optional end walls 1023 (only depicted in the embodiment of FIGS. 10G and 10H), an inner surface 1014, an outer surface 1015, and rolled end crimps 1022 to sealingly close one or both ends of the bag 1012. The sidewalls 1013 are typically formed with expandable pleats to allow the bag 1012 to expand to inflate to a large volume capacity during use, yet efficiently fold compactly for packaging and shipping to the consumer. The sidewalls 1013 and/or end walls 1023 comprise an air-permeable filtering material that allows air to pass through them, but captures dirt and debris within the enclosure formed by the walls. Bag filters and the materials from which they can be made are well known in the art, and as such a detailed discussion of them is not necessary here. It will be understood that the present invention may be used with any kind bag filter, including those having paper walls, non-woven walls, and so on.

A flange 1020 is adhered to an opening in the bag 1012 to form an inlet 1016. The flange 1020 adds stability to the inlet 1016 and further assists in sealing the bag 1012 to the vacuum cleaner. The flange 1020 is preferably made from cardboard, paperboard, or plastic. The flange 1020 and inlet 1016 may be placed on a sidewall 1013 (FIGS. 10A-10F) or an end wall 1023 (FIGS. 10G and 10H). Furthermore, an annular rubber seal (not shown) may be provided at the inlet 1016 to assist with sealing the bag to the vacuum mounting tube. Such seals are generally known in the art, and may comprise a soft, resilient material that elastically surrounds a mounting tube onto which the inlet is placed, such the mounting tube 115 shown in FIG. 1. Other flange features may include lock-out tabs that engage with a mechanism that prevents closure and/or of the vacuum cleaner when the filter bag is not in place, handles to facilitate bag installation and/or removal, and inlet closure doors that slide or pivot in place to cover the inlet 1016 when the bag 1012 is removed from the vacuum cleaner.

The sodium bicarbonate sheet 1000 may simply be placed inside the bag filter 1012, but more preferably is adhesively bonded or sewn to the inner surface 1014 of the bag filter 1012. The location and air permeability of the sheet 1000 can be modified to obtain several expected beneficial results. In a preferred embodiment, the sheet 1000 is adhered to the inner surface 1014 with an air-impermeable adhesive that covers about 5%, to about 20% of the sheet area, and most preferably about 6% of the sheet area. In this embodiment, the sheet 1000 is preferably substantially air permeable, to generally reduce the bag's overall resistance to air flow, but it is believed that the use of substantial area of air-impermeable adhesive will block some airflow to deflect the air through the plane of the sheet to agitate the sodium bicarbonate and release it into the bag 1012. Alternatively, the sheet 1000 may be mostly or completely air-impervious, or provided with an air impermeable backing, which would increase the bag's overall airflow resistance, but is expected to cause the incoming air to strike and travel along the sheet to better distribute the sodium bicarbonate into the bag's interior.

As shown in FIGS. 10A-10D, the sheet 1000 is preferably attached immediately opposite the air inlet 1016 into the bag filter 1012, so that the incoming air flow 1018 strikes the sheet 1000 and mixes with the sodium bicarbonate or other chemicals in the sheet 1000. In this way, the sheet 1000 acts as a sacrificial element that is replaced with each replacement of the bag filter 1012. Also in this embodiment, the sheet 1000 may be formed of or layered with an anti-penetration barrier (not shown) to help prevent objects carried by the incoming airstream from penetrating the bag filter 1012. Examples of such materials are shown in U.S. Pat. No. 5,690,711, which is incorporated herein by reference. In a preferred embodiment, the anti-penetration layer comprises a relatively tough material, such at TYVEK™ (a web of high-density polyethylene fibers that are arranged in a random, non-directional manner), to help protect the filter bag 1012 from being punctured by hard objects that may enter the filter bag 1012. The sheet 1000 may also comprise a foam material or layer, or other lofty material, which may prevent bag penetration by cushioning incoming objects before they strike the bag inner surface 1014. The anti-penetration barrier, if one is used, is preferably positioned immediately adjacent the inner wall of the bag filter.

In a preferred embodiment, such as the ones in FIGS. 10A-10H, a single sheet 1000 formed of one or more overlapping sheet layers and sodium bicarbonate particles is positioned in the bag filter 1012. In another preferred embodiment, one or more sheets 1000 may be used, but they cover less than about 30% of the bag filter's working surface area (that is, the area of the bag filter walls through which air generally passes in use, which excludes the surface covered by the flange and rolled pleated ends, but includes the area covered by the sheet 1000 itself), and more preferably less than about 25% of the working surface area. In even more preferred embodiments, the sheet 1000 or sheets cover about 4-15% of the bag filter's working surface area. The foregoing constructions are believed to improve upon the prior art, which has used numerous attached sheets that cover the majority of the bag's working surface or has treated the filter walls themselves with deodorants. In contrast, the foregoing embodiments do not require the filter walls themselves to be treated with deodorizing compound, do not require multiple separate sheets (if a single sheet is used) to be attached, both of which increase the overall expense of the device. Furthermore, it has been discovered that using deodorizing sheets that cover less of the filter bag, rather than more (as appears to be the trend in the prior art), actually provides suitable deodorizing both during use and during latent periods. As such, the foregoing embodiments of the present invention provide a single sheet (or multiple small sheets) over a relatively small area, which eases manufacturing requirements, reduces raw material costs (including, for example, costs of the sheet substrate, sodium bicarbonate, and adhesive or other bonding devices), and still provides a noticeable odor reduction in the vacuum cleaner. Despite the expected advantages of the foregoing embodiments, other embodiments of the invention provide separate and distinct advantages over the prior art, and such embodiments may use multiple separate or overlapping deodorizing sheets in a single bag filter 1012, and they may exceed the coverage percentages listed above.

Figure 10A:
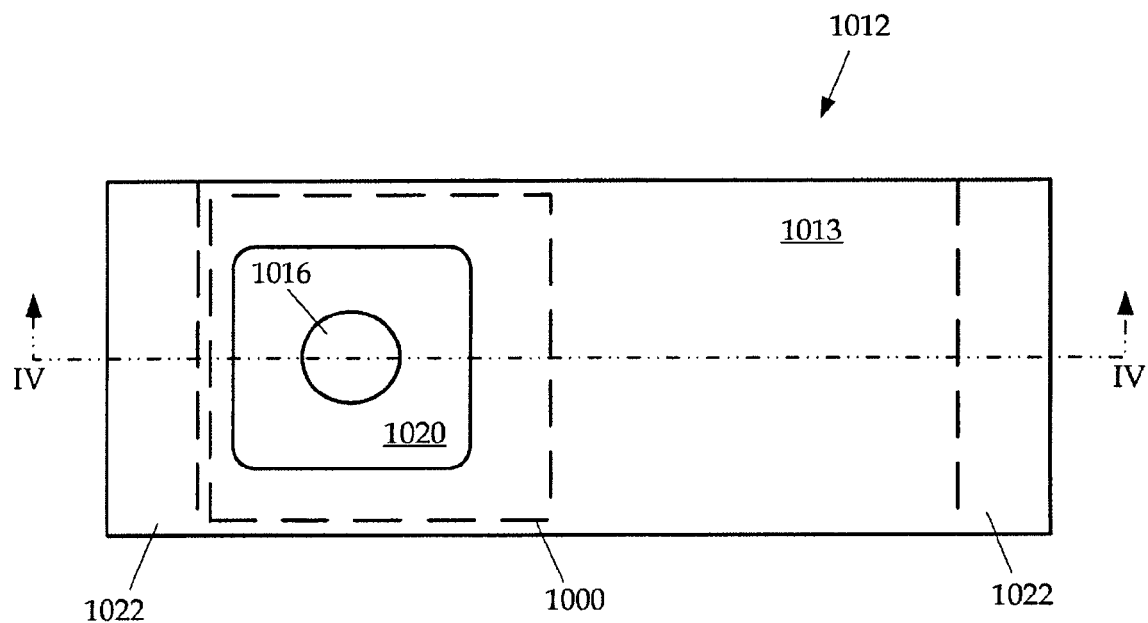
FIG. 10A is an embodiment of a chemically-impregnated deodorizing sheet of the present invention pre-installed in a conventional bag-type filter.
Figure 10B:
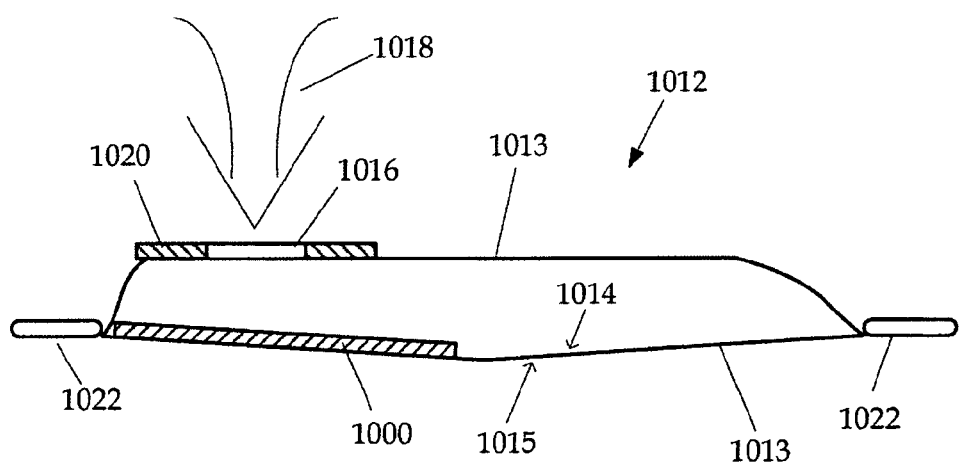
FIG. 10B is a cross-sectional view of the embodiment of FIG. 10A, shown along line IV-IV thereof.
Figure 10C:
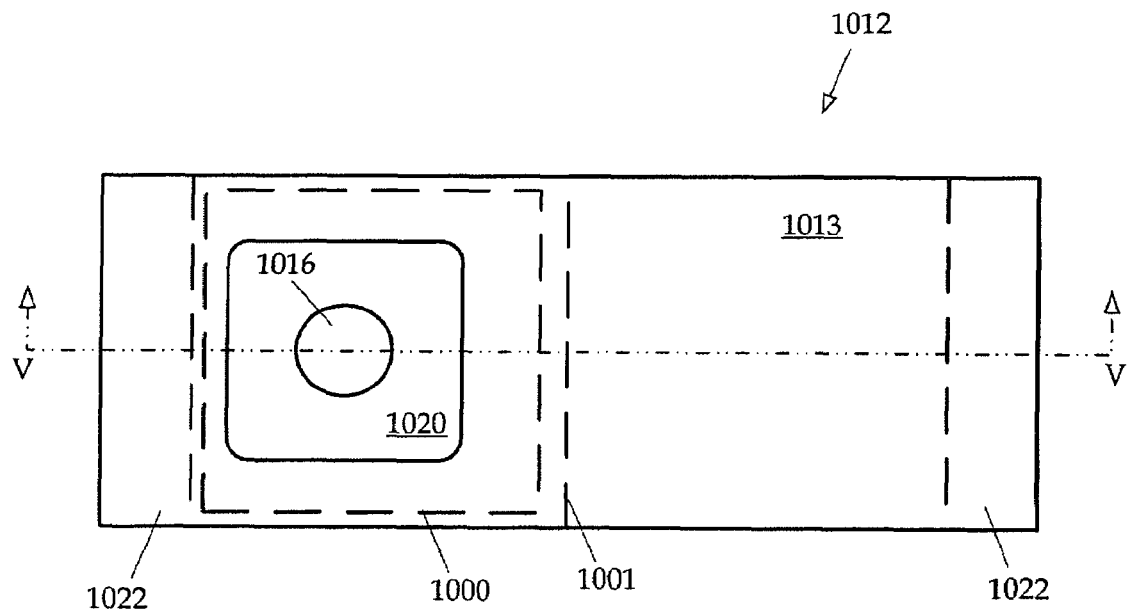
FIG. 10C is an embodiment of a chemically-impregnated deodorizing sheet of the present invention pre-installed in a conventional bag-type filter.
Figure 10D:
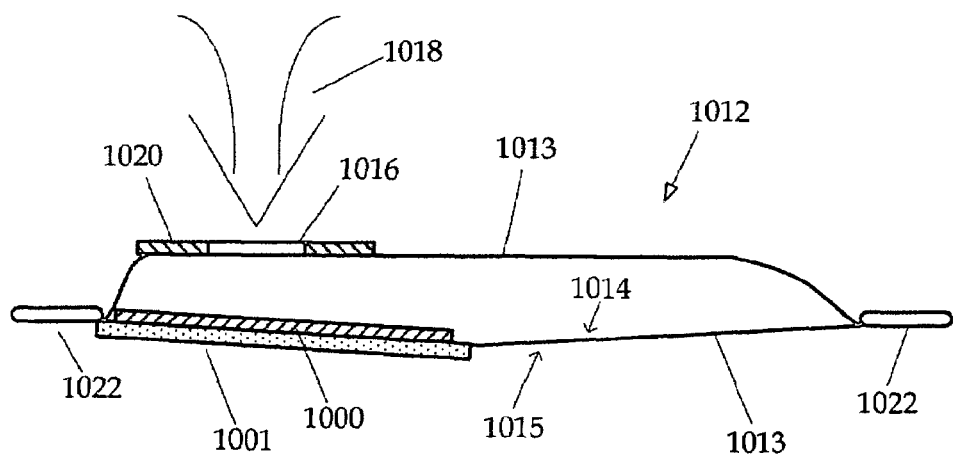
FIG. 10D is a cross-sectional view of the embodiment of FIG. 10C, shown along line V-V thereof.

Referring specifically to FIGS. 10C and 10D, another preferred embodiment may also include an air restricting layer 1001 on the inner surface 1014 or, more preferably, the outer surface 1015 of the bag 1012 overlying the sheet 1000. In the preferred embodiment, the restricting layer 1001 is a blocking emulsion printed in a dotted pattern on the outer surface 1015, but may take other forms such as adhered paper, cardboard, metal foil or plastic laminate, or a simple application of adhesive, any of which may be perforated to allow some air-permeability. The air restricting emulsion 1001 of the preferred embodiment reduces airflow through sheet 1000 by approximately 30% to 90%, and more preferably about 60% to about 70%, and most preferably about 66%. But more or less restriction may be desirable, and it may even be desirable to have up to 100% restriction. The air restricting layer 1001 may be removable to allow the user to control, to some degree, the airflow through the deodorant sheet 1000, but it is more preferred for the air restricting layer 1001 to be permanently attached.

In operation, the incoming stream of dust-laden air 1018 enters the dustbag 1012, and strikes the sheet 1000. The restricting layer 1001 redirects some or all of the air to the bottom of the bag 1012. The turbulent airflow created by this drastic airflow redirection dislodges the active ingredients of the deodorizing mix from the sheet 1000, and allows the sodium bicarbonate and other deodorizing agents to more readily mix with the air and dust. Such dislodged particles remain in contact with the dust while the vacuum sits idle, increasing the effectiveness of the deodorizers. This is useful because a vacuum's idle time is typically much greater than its operational time.

Referring to FIGS. 10E-10H, another embodiment of the present invention comprises a sheet 1000 at or near the bottom of the bag 1012—that is, at the bottom of the bag 1012 as it is oriented when mounted in a vacuum cleaner. This places the sodium bicarbonate and other active ingredients in the sheet 1000 in close proximity to the dust and debris in the bag 1012, and promotes odor neutralization during idle time.

Figure 10E:
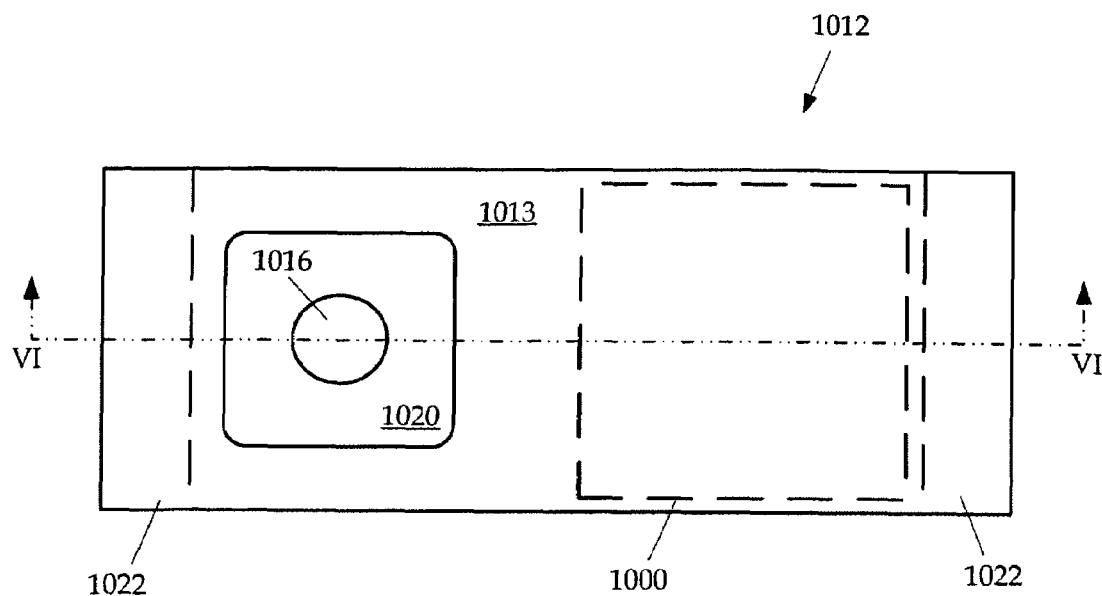
FIG. 10E is an embodiment of a chemically-impregnated deodorizing sheet of the present invention pre-installed in a conventional bag-type filter.
Figure 10F:
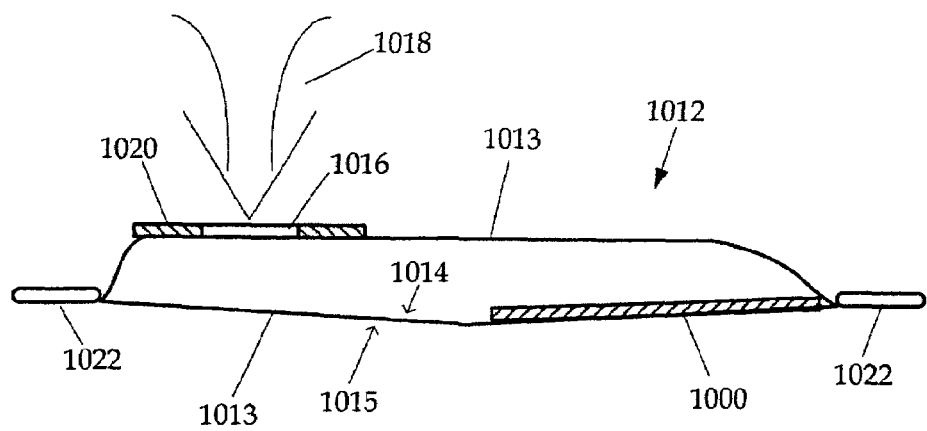
FIG. 10F is a cross-sectional view of the embodiment of FIG. 10E, shown along line VI-VI thereof.
Figure 10G:
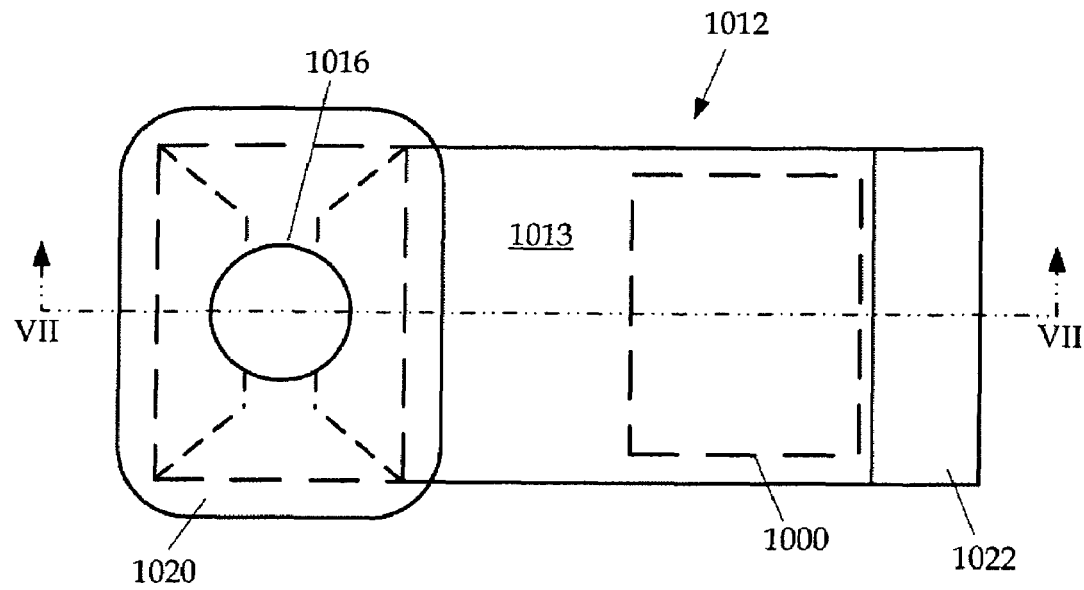
FIG. 10G is an embodiment of a chemically-impregnated deodorizing sheet of the present invention pre-installed in a conventional bag-type filter.
Figure 10H:
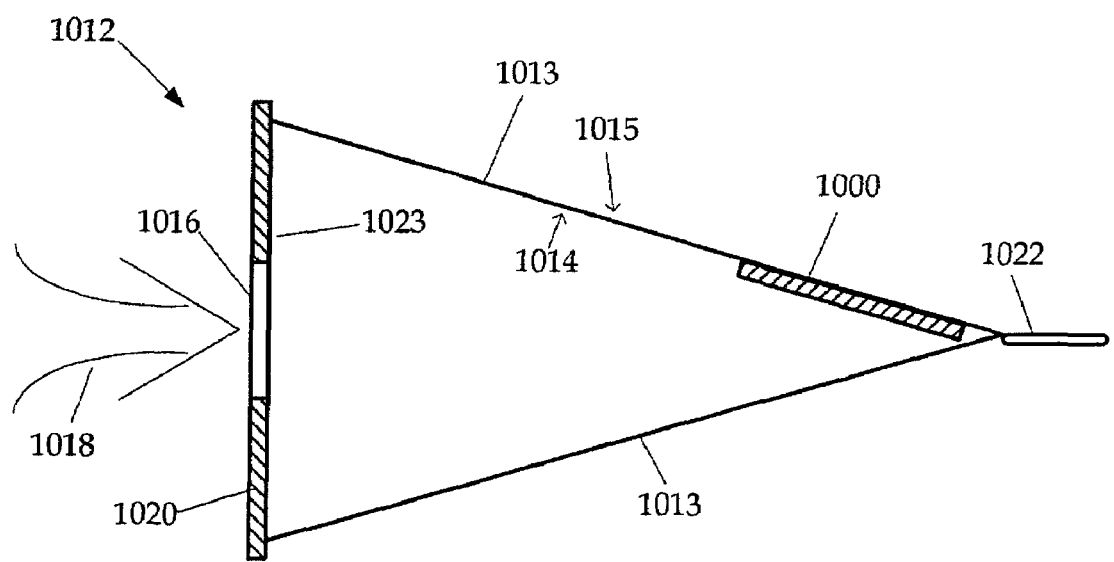
FIG. 10H is a cross-sectional view of the embodiment of FIG. 10G, shown along line VII-VII thereof.

In the embodiment of FIGS. 10E and 10F, the bag 1012 comprises a two-paneled construction formed by two sheets with the flange 1020 located on the side of the bag 1012. The embodiment of FIGS. 10G and 10H is similar, but uses a three paneled construction with the flange 1020 located at the end of the two side sheets.

Figure 11A:
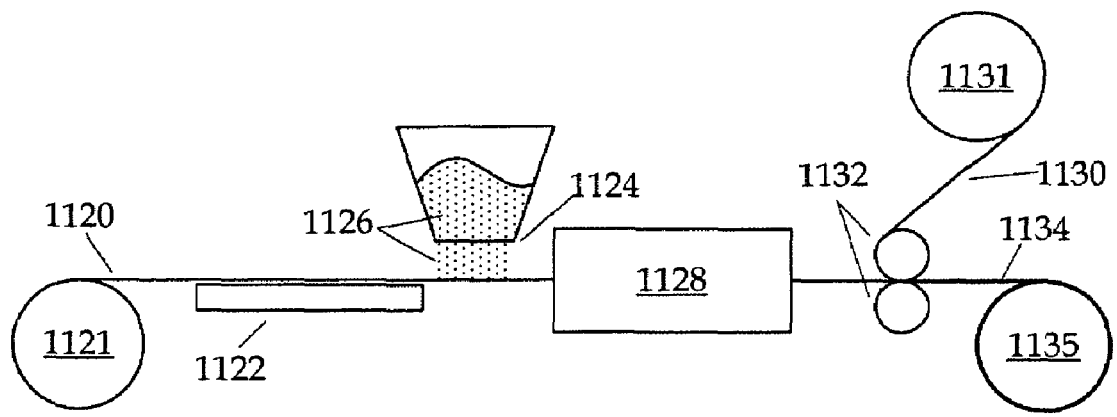
FIG. 11A is an embodiment of a method of manufacturing one embodiment of a chemically-impregnated deodorizing sheet.
Figure 11B:
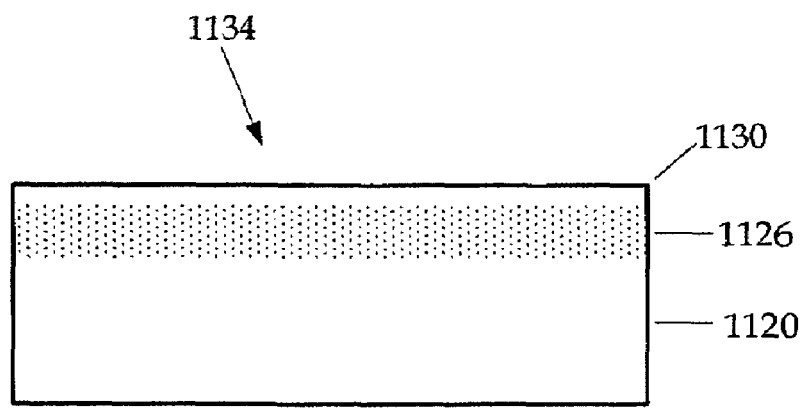
FIG. 11B illustrates the chemically-impregnated sheet made from the process depicted in FIG. 11A.

A preferred embodiment for producing an impregnated sheet for use with the present invention is depicted in FIGS. 11A and 11B. The sheet 1134 produced by this process comprises first and second sheets 1120, 1130 and a dry deodorizing mixture 1126. The deodorizing mixture 1126 comprises a blend of deodorant, adhesive, and other useful compounds, if desired. In a preferred embodiment, the deodorizing mixture 1126 is a deodorizer comprising of 91.5 wt. % (weight percentage) sodium bicarbonate, such as ARM & HAMMER™ baking soda (with grades 2 and 5 being particularly useful), 5.0 wt. % 11P23 hot melt adhesive manufactured by EMS Griltech of Sumter, S.C. ("GRILTEX™ hotmelt"—a heat-resistant, polymer-containing, solvent-free binder), and 3.5% wt. % MOLSIV™ Adsorbents Smell Rite® Zeolite manufactured by UOP L.L.C. of Des Plaines, Ill. (a synthetic sodium aluminum silicate with a zeolite structure that has been treated to be adsorptive of odoriferous compounds, and has organophilic micropores that attract and trap odor molecules). The deodorizing mixture 1126 may be mixed in a pre-cleaned ribbon mixer or other suitable high shear powder mixer for sufficient time to fully blend the chemicals.

Other useful compounds that may be used with the present invention include, but are not limited to, activated carbons, activated charcoal, diatomaceous earths, cyclodextrin, quaternary ammonium salts, silane quaternary ammonium salts, clays, fragrance oils, and the like. Suitable mixtures include, for example, about 50-100 wt. % (weight percentage) of sodium bicarbonate, about 0-10 wt. % of zeolites, about 0-20 wt. % of activated carbon, about 0-5 wt. % of quaternary ammonium salts, about 0-5 wt. % of silane quarternary ammonium salts and about 0-2 wt. % of fragrance oils. In a preferred embodiment, the adhesive may be provided as about 2-6 wt. % of the deodorant composition, but may alternatively be provided as about 5-15 wt. %, and more preferably about 5-10 wt. % to better adhere the deodorizing particles to the sheets and adhere the sheets to one another.

The first non-woven sheet 1120 preferably comprises a non-woven polyester sheet with a thickness of 1.88 mm. Such a sheet is sold as style PN 232 by the Precision Custom Coatings Company of Totowa, N.J. Other suitable sheet materials may have a thickness of about 0.05 to 6.00 mm and a basis weight of about 25 to 200 gsm (grams per square meter). More preferably, the first sheet 1120 is about 0.50 to 4.00 mm thick, or even more preferably about 1.00 to 3.00 mm thick. Suitable alternative materials include, for example, natural fibers, other synthetic fibers, or open cell foams. The sheet is provided as a roll 1121 (as shown), as separate sheets, or manufactured from raw materials on the manufacturing line itself. When provided in a roll 1121, the sheet 1120 may be passed through a sheet spreader 1122, which pulls the sheet 1120 laterally, to make the sheet taut. The sheet 1120 then passes under a sifter 1124, or other type of deposition device, such as a vibratory feeder, which deposits the sodium bicarbonate deodorizing mixture 1126 onto the sheet 1120. It has been found that a portion of the mixture 1126 sinks down into the thickness of the sheet 1120, but much of it remains at or near the sheet's surface.

The sheet 1120, with the deodorizing mixture 1126 sifted onto it, then passes through a curing oven 1128. Heating lamps, hot air, or any other suitable heat source may be used in the oven 1128. The oven 1128 heats the surface of the sheet 1120 to melt the hot melt adhesive in the mixture 1126 and thereby bind the sacrificial deodorizing elements of the deodorizing mixture 1126 to the sheet 1120. A suitable temperature for the process is a sheet surface temperature of about 100° F.-300° F., and more preferably about 270° F. or 280° F.-300° F. The foregoing temperatures have been found to be suitable to bind the deodorizing compounds in place without damaging them or the sheet 1120, and without unduly coating the deodorizing compounds with adhesive.

It will be understood that the temperature and length of time in the oven can be adjusted to obtain the most favorable coating of the hot melt adhesive on the deodorant components and the sheet 1120. Too much heat may result in damage to the sheet 1120 or deodorants, or may cause excessive coating of the deodorant by the adhesive. Too little heat may result in insufficient binding of the deodorant. Preferably, the sheet 1120 is exposed to the heat just long enough to obtain a surface temperature of about 270° F. or 280° F. to 300° F., but this target temperature may vary depending on the type of sheet material or amount or composition of the deodorizing mixture 1126. This target temperature can be varied by any suitable means, such as varying the line speed, oven length, oven temperature, and so on, as will be appreciated by those of ordinary skill in the art.

After the first sheet 1120 emerges from the oven 1128, a second sheet 1130 is laid on the first sheet 1120 to overlie the deodorizing mixture 1126. The second sheet 1130 is provided to help capture the deodorizing mixture 1126 in place and reduce the dustiness of the finished product 1134 but is air permeable to allow airflow to the deodorizing mixture 1126. In the preferred embodiment, the second sheet 1130 comprises a PES (polyethersulfone) and rayon scrim with a thickness of about 0.203 mm. The Precision Custom Coatings Company of Totowa, N.J., sells such a sheet as style PC 858. This second sheet 1130 is unwound from a roll 1135 and pressed onto the first sheet 1120 and deodorizing mixture 1126 after it emerges from the oven 1128, and while it is still warm. Rollers 1132 compress the two sheets together at a pressure of about 50-200 pounds per square inch of pressure, and more preferably about 80 pounds per square inch. By applying the second sheet 1130 immediately downstream of the oven 1128, it can be held in place by the still-warm hot melt adhesive, an no additional adhesive is required. Of course, a separate adhesive may be used to supplement the hot melt adhesive, or if it is desired to apply the second sheet 1130 at a location where the hot melt adhesive in the deodorizing mixture 1126 is not longer warm.

As the adhesive cools, it adheres the two sheets 1120, 1130 and the deodorizing mixture 1126 together. The finished product 1134 is about 0.50-5.00 mm thick, and more preferably about 2 mm thick (with potential for significant variation caused by the handling process and due to variations in the sheets' starting thickness and processing), with 3 layers: the first sheet 1120, the deodorizing mixture 1126, and the second sheet 1130. FIG. 11B depicts these 3 layers. It will be appreciated that, while FIG. 11B shows the layers as being discrete, some intermingling may occur in practice, and up to 100% diffusion (i.e., uniform diffusion) of the deodorizing mixture 1126 into the first and/or second sheet 1120, 1130 may be accomplished and used with the invention, if desired. To obtain such high penetration, however, other manufacturing methods may be necessary. Examples of other suitable methods for impregnating a material to form sodium bicarbonate sheet are disclosed in U.S. Pat. Nos. 6,099,101, and 6,302,946, which are incorporated herein by reference.

The process ends with the final product 1134 being rolled onto a final roll 1135. This product 1134 may now be cut into various shapes and sizes and utilized as described herein, preferably, but not necessarily, with the second sheet 1130 facing inwards into the bag filter. The finished product 1134 is preferably cut with an ultrasonic, thermal, or other self-sealing process. A self-sealing process binds the layers of the sheet together at the cut, and thus ensures minimal loss of the deodorizing mix 1126 after cutting. If a self-sealing method is not employed, then the amount of deodorizing mix 1126 may be increased, preferably by about 5% to 10% to account for the losses that may occur in the manufacturing process, and/or the amount of adhesive may optionally be increased to about 5-15 wt. %, and more preferably to about 5-10 wt. % to ensure sealing of the sheets and adherence of the deodorizing composition.

The size of the finished sodium bicarbonate impregnated sheet will vary, depending on the amount of dirt that is expected to accumulate in the particular application in which the sheet is used. Larger sheets generally would be used when greater amounts of dirt are expected to accumulate. Deodorizing sheets made from the previously described process have been found to be effective in reducing the odor released from a vacuum cleaner when cut to sizes ranging from 16 in$^2$ to 40 in$^2$ and when used to replace a standard filter used in a bagless vacuum dustcup. Smaller sheets, as small as 2 in$^2$ or even smaller, may be effective in small handheld vacuums, and much larger sheets may be used in large-capacity shop vacuums and central vacuums. It is believed that in applications in which the sheet is used within a dirt container (as opposed to being outside the actual dirt container, as in the case of sheets used, for example, with post-motor filters) there is a directly proportional relationship between the size of the dirt container and the size of the sheet necessary to provide effective odor prevention.

A preferred embodiment, such as one that is preferred to be used with the embodiments of FIGS. 10A-10H, has approximately 10 ounces of deodorizing mixture 1126 per square yard of sheet, or 10 oz/yd$^2$. The amount of deodorizing mixture 1126 per square yard of sheet is determined by the following equation:

$$\text{Load (oz/yd}^2\text{)} = \frac{\text{Spread Rate (oz/min)}}{\text{Fabric Speed (yd/min)} * \text{Fabric Width (yd)}}$$

"Load" represents the amount of deodorizing mixture per square yard of sheet with 10 oz/yd$^2$ being the preferred amount. "Spread Rate," expressed in oz/min, represents the rate the deodorizing mixture 1126 is spread onto the non-woven sheet 1120. "Sheet Speed" is the linear speed the sheet 1120 passes under the sifter 1124, and is expressed in yd/min. Finally, "Sheet Width" is the lateral width of the sheet as expressed in yards. Given the equation above, one skilled in the art can determine the parameters required to deposit 10 oz of mixture 1126 onto 1 square yard of sheet. One embodiment provides a spread rate of 40 oz/min, which would require a sheet speed of 4 yds/min for a 1 yd wide sheet.

Figure 12A:
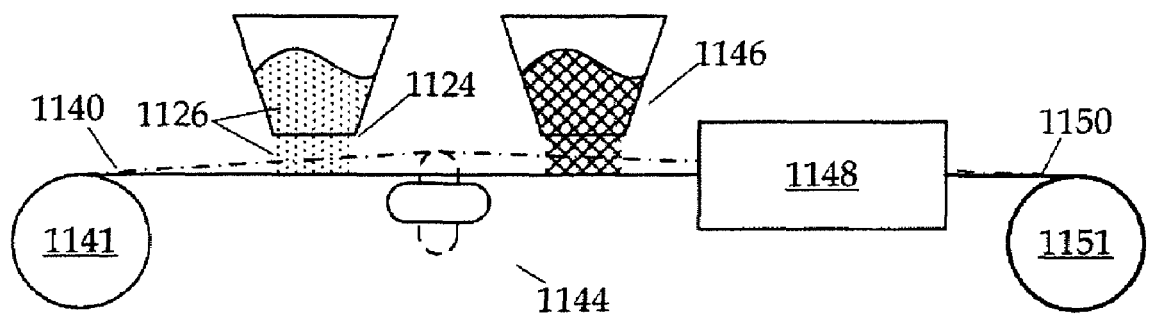
FIG. 12A is another embodiment of a method of manufacturing another embodiment of a chemically-impregnated deodorizing sheet.
Figure 12B:
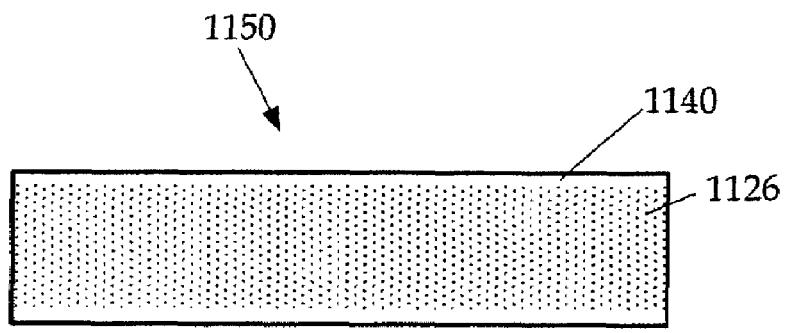
FIG. 12B illustrates the chemically-impregnated sheet made from the process depicted in FIG. 12A.

Referring now to FIGS. 12A and 12B, another process to manufacture a chemically impregnated sheet is described. This embodiment starts with a roll 1241 of non-woven sheet 1240. The sheet 1240 first passes under a sifter 1224, which deposits an even layer of deodorizing mixture 1226 on the sheet 1240. In this embodiment, the deodorizing mixture 1226 includes sodium bicarbonate, a water soluble adhesive, and any other useful deodorants or fragrances, if desired. The sheet 1240 and deodorizing mixture 1226, then pass over a rotating cam 1244. The cam 1244 continuously rotates through 360° about an axis that is parallel to the plane of the sheet and perpendicular to the path of the sheet. The cam 1244 has one or more eccentric lobes that strike the sheet 1240 and impart vibrations thereto to work the mixture 1226 into the sheet 1240 fibers. The cam 1244 of FIG. 12B has two lobes, and is shown in two different positions representing the two extremes through which the cam 1244 rotates. When the cam 1244 is in a first position, it is in light contact or out of contact with the sheet 1244. When the cam 1244 rotates to a second position, shown in phantom lines, it presses against and displaces the sheet 1240. Thus, as the cam 1244 rotates, it pushes the sheet up and down and generally creates a first order standing wave with stationary nodes located at the sheet rolls 1241, 1251 at each end of the process. Other embodiments may include more cams, cams having a varied number of lobes, cams with lobes of varying dimension, cams placed on top of the sheet, and cams with constant or variable rotational speeds. Pinch rollers may also be provided to isolate the vertical displacement caused by the cam 1244.

After the deodorizing mixture 1226 is applied to the sheet 1240 and agitated into the sheet 1240 by the cam 1244, the sheet 1240 and mixture 1226 pass under a hot water vapor mist 1246 or a warm water spray. The water or water vapor mist 1246 emulsifies the adhesive so that the adhesive bonds the sodium bicarbonate to the fibers of the non-woven sheet 1240. After being impregnated with sodium bicarbonate in this manner, the sheet 1240 passes into an oven (as shown above) or under a fan 1248, which may also have an air heating element, to evaporate excess moisture and dry the impregnated material. As the adhesive cools and dries, it bonds the deodorizing elements of the mixture 1226 to the sheet 1240 and creates an impregnated sheet designated as 1250. Sheet 1250 is collected onto a final roll 1251, and may now be cut into various shapes and sizes and utilized as described herein. A cross-section of the sheet 1250 is illustrated in FIG. 8D with the mix 1226 dispersed within the sheet 1240.

It should be noted that in the foregoing embodiment, the hot water vapor step 1246, may be omitted if the operation of the cam 1244 is suitable to obtain the desired penetration of the mixture 1246 in the sheet 1240.

It will be understood that the foregoing embodiments are exemplary only, and variations of these embodiments and other embodiments will be apparent to those of ordinary skill in the art in light of the teachings provided herein. In addition, it may be possible to mix the steps of the two processes described herein. As an example, the rotating cam 1244 of FIGS. 12A and 12B may also be used with the embodiments of FIGS. 11A and 11B. It will be understood that the foregoing depictions of manufacturing systems and procedures are not intended to be exclusive of other features and steps. For example, either of the foregoing embodiments may include additional features such as loose powder recovery systems, vacuum assisted particle penetration devices that draw a vacuum on one side of the sheet to pull the particles deeper into the sheet, accumulators, and so on.

Figure 13A:
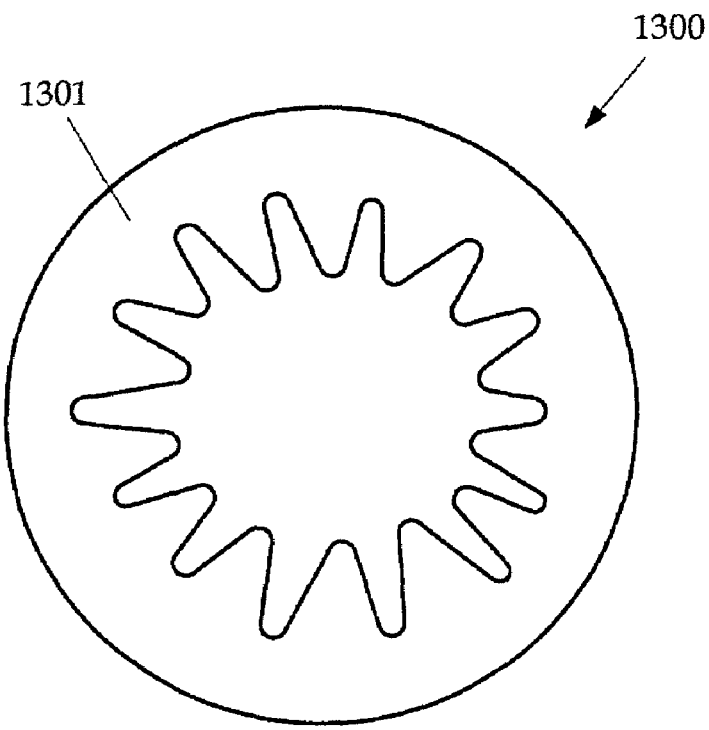
FIG. 13A is an embodiment of a disk-shaped chemically-impregnated article of the present invention.
Figure 13B:
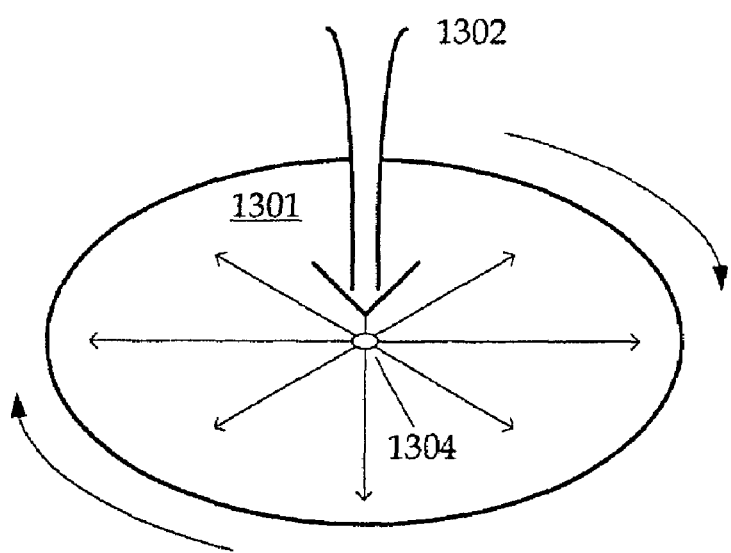
FIG. 13B illustrates the process used to create the embodiment of FIG. 13A.

Referring now to FIGS. 13A-13C, another embodiment of a chemically impregnated sheet is depicted as disk 1300. Disk 1300 is circular and formed from open cell foam, non-woven high loft fabric 1301, or other materials, and can be used in the same way as other sodium bicarbonate-impregnated sheets described herein.

To manufacture this embodiment, the disk 1300 is spun horizontally at a high rotational speed, while a sodium bicarbonate slurry 1302 is added to the disk center 1304, which is located at the vertical axis of rotation. The resulting centrifugal force slings the slurry away from the center 1304, as shown by the arrows, and distributes the slurry 1302 throughout the disk 1300. After the slurry 1302 is sufficiently distributed, the disk 1300 may be further spun to sling out excess water and assist with drying. Additional or alternative methods of drying the disk 1300 may include subjecting the disk 1300 to a heat source, forced-air convection, or a combination thereof.

Preferably, the sodium bicarbonate is dyed yellow, and the disk fabric 1301 is white, to provide a distinctive and unique appearance.

Referring to FIG. 13C, a variation of the embodiment of FIG. 13A, also includes activated carbon 1311. The activated carbon 1311 preferably is provided in a slurry 1312 and applied around the perimeter of the disk to create a distinctive and unique appearance. Alternatively, the activated carbon 1311 may be added to the sodium bicarbonate slurry 1302, or may be diffused, as described above, in a separate sheet disk and adhered to disk 1300.

Slurries 1302, 1312 may also be provided with a hot melt adhesive, similar to the hot melt adhesive contained in mix 1126. If a hot melt adhesive is provided, then it will also be necessary to subject disks 1300, 1310 to a heat source, such as a forced-air convection oven, to activate the adhesive. This heating process would be similar to the oven process 1148 shown and described in FIG. 8C and accompanying text. Alternatively, the slurry may be heated before being applied.

Other methods will be readily apparent to those of ordinary skill in the art in view of the present disclosure, and such other methods are included within the scope of the invention. Non-limiting examples of such variations include forming the sodium bicarbonate sheet as a layered non-woven material having powdered sodium bicarbonate distributed between or within the layers, or coating a sheet with sodium bicarbonate on its exterior surfaces.

EXAMPLE 1

Tests were conducted using Eureka Model 402 vacuum cleaners. The Eureka Model 402 vacuum cleaners were bagless and contained a cone shaped filter within the dust cup. A control filter was compared to a treated filter. The control filter was a standard untreated filter. The treated filter contained the deodorizing device of the present invention.

The deodorizing device included the deodorizing composition disposed between two nonwoven gas porous materials. The deodorizing composition contained about 91.5% sodium bicarbonate, 3.5% zeolite and 5% adhesive (GRILTEX™) and was coated on a 6.25 in.×6.25 in. size filter at a coating level of 8.7 oz/yd$^2$, (0.19 g/in$^2$). The first nonwoven material was a moldable polyester having a fabric weight of 3.2 oz/yd$^2$ (108.5 g/m$^2$); tensile strength in the machine direction of 25 lbs; tensile strength in the cross-machine direction of about 75 lbs; and thickness of 74 mils (1.88 mm). The first non-woven material served as the bottom layer of the deodorizing device and was a heavier sponge-like nonwoven material than the top layer. A suitable example of the first nonwoven material was obtained under the trade designation PN232 available from Precision Custom Coatings LLC, Totowa, N.J.

The second nonwoven material used herein was a hydrophilic PES/rayon having a fabric weight of 0.75 oz/yd$^2$ (25.4 g/m$^2$); tensile strength in the machine direction of 10.8 lbs; tensile strength in the cross-machine direction of 0.5 lbs; and thickness of 8 mils (0.203 mm). The second nonwoven material served as the top layer of the deodorizing device. The second nonwoven material was a "scrim" that minimized dustiness of the product and allowed for good air flow. A suitable example of the second nonwoven material was obtained under the trade designation PC757, available from Precision Custom Coatings LLC, Totowa, N.J.

Each of the filtered dust cups was filled with soil that was enhanced to emit a noticeable household odor. The soil consisted of 50 grams of damp vacuum cleaner dust, 2.5 grams of cat urine (provided by Martin Creek Kennels, of Williford, Ark.), and 1.25 grams of Limburger cheese. The cat urine provided a strong, characteristic pet odor and the Limburger cheese imitated human body odor and strong kitchen odors.

The Eureka Model 402 machines were equally loaded with soils and allowed to sit for 4 hours, and then placed inside cleaned new 30 gallon plastic garbage cans. The cans were used to contain the air emitted from the exhaust of the vacuum. The plastic lids on the garbage cans had sniffing ports cut into them through which panelists could sample the air therein.

After the 4 hour gestation time, the lids were sealed and the vacuums were activated for 5 seconds. The air ejected in this 5 second period represents the most odorous air, usually encountered at machine startup. It was captured in the cans for panelists to sample.

Twenty panelists rated the two cans on a 0 to 6 scale for malodor. A rating of 0 represented the least odor, a rating of 6 represented the most odor. The following table shows the result from two separate trials:

TABLE 1

| Trial | Control | Treated |
|---|---|---|
| #1 | 3.6 | 1.4 |
| #2 | 3.8 | 1.1 |

In the test, the difference between the heated and control was statistically different at the 99% confidence level.

EXAMPLE 2

Odor levels were measured in a sensory panel comparing a control sample to two treated samples. The odor studied in this test was 100 grams of damp vacuum cleaner dust. The tests were conducted by disposing the odors inside a 2 quart enclosed space.

The control sample had only the odor in the container. The two treated samples had the odors in the container and the deodorizing devices of the present invention where 7.4 grams of the deodorizing composition were loaded between two 6.25 in. square pieces of nonwoven material. The first "treated" sample contained 88% sodium bicarbonate, 7% Smellrite@, and 5% GRILTEX™ hotmelt on the nonwoven material. The second "treated" sample contained 91.5% sodium bicarbonate, 3.5% zeolite and 5% adhesive on the nonwoven material.

Eighteen panelists smelled the odor inside the 2-quart enclosed space and rated the smells on a 0 to 6 scale for malodor. A rating of 0 represented the least odor, a rating of 6 represented the most odor. The following table shows the result from the present test:

TABLE 2

| Sample | Odor Level |
|---|---|
| Control | 4.2 |
| Treated Sample #1 | 2.8 |
| Treated Sample #2 | 2.4 |

There was no statistically significant difference between the two samples and both of the treated samples had a statistically significant lower odor source than the control.

It should be understood that the foregoing embodiments are exemplary only, and other embodiments will be apparent to those of ordinary skill in the art in light of the teachings provided herein. Furthermore, while the foregoing description illustrates the use of various embodiments of sodium bicarbonate chemical neutralizers in use with various different types of cleaning device, it will be understood that the embodiments described with respect to each device may also be used with the other types of the device. For example, the sleeve 122 described with respect to the bagless vacuum in FIG. 1 could be used in conjunction with the bagless vacuum of FIG. 2A, or the extractor of FIG. 4A. Other variations will be apparent to those of ordinary skill in the art in view of the present disclosure and with practice of the invention.

We claim:

1. A vacuum cleaner bag filter comprising:
    one or more filter walls forming a generally air permeable enclosure having a bag opening therethrough, the one or more filter walls having a working surface area through which air can pass during use;
    a flange attached to the one or more filter walls to cover the bag opening, the flange comprising a relatively rigid structure having an air inlet passing into the air permeable enclosure;
    a deodorizing sheet attached to an inner surface of the one or more filter walls, the deodorizing sheet comprising:
    a first sheet layer, and
    a plurality of sodium bicarbonate particles operatively associated with the first sheet layer; and
    wherein the deodorizing sheet covers less than about 30% of the working surface area.

2. The vacuum cleaner bag filter of claim 1, wherein the deodorizing sheet further comprises a second sheet layer, and the plurality of sodium bicarbonate particles are generally deposited between the first sheet layer and the second sheet layer.

3. The vacuum cleaner bag filter of claim 2, wherein the sodium bicarbonate particles are adhered to at least the first sheet layer by a hot melt adhesive.

4. The vacuum cleaner bag filter of claim 2, wherein the sodium bicarbonate particles are non-uniformly distributed throughout the thickness of the deodorizing sheet.

5. The vacuum cleaner bag filter of claim 2, wherein the sodium bicarbonate particles are uniformly distributed throughout the thickness of the deodorizing sheet.

6. The vacuum cleaner bag filter of claim 2, wherein the first sheet comprises a non-woven sheet, and the second sheet comprises a scrim layer.

7. The vacuum cleaner bag filter of claim 6, wherein the sodium bicarbonate particles and second sheet layer are adhered to the first sheet layer by a hot melt adhesive.

8. The vacuum cleaner bag filter of claim 1, wherein the deodorizing sheet is positioned on the one or more filter walls at a location opposite the air inlet, such that air entering the air inlet impinges upon the deodorizing sheet.

9. The vacuum cleaner bag filter of claim 8, the deodorizing sheet further comprises a second sheet layer, the second sheet layer comprising an anti-penetration barrier to help prevent incoming objects from penetrating the one or more filter walls.

10. The vacuum cleaner bag filter of claim 1, wherein the deodorizing sheet covers less than about 25% of the working surface area.

11. The vacuum cleaner bag filter of claim 1, wherein the deodorizing sheet covers about 4% to about 15% of the working surface area.

12. The vacuum cleaner bag filter of claim 1, wherein the deodorizing sheet is attached to the one or more filter walls by an air-impervious adhesive that covers at least about 5% of the surface area of the deodorizing sheet.

13. The vacuum cleaner bag filter of claim 1, further comprising an air restricting layer attached to the outer surface of the one or more filter walls and overlying the deodorizing sheet.

14. The vacuum cleaner bag filter of claim 13, wherein the air restricting layer comprises a blocking emulsion printed on the outer surface of the one or more filter walls.

15. The vacuum cleaner bag filter of claim 13, wherein the air restricting layer reduces airflow through the deodorant sheet by about 30% to about 90%.

16. The vacuum cleaner bag filter of claim 13, wherein the air restricting layer reduces airflow through the deodorant sheet by about 60-70%.

17. The vacuum cleaner bag filter of claim 1, wherein the deodorizing sheet comprises a single deodorizing sheet.

18. The vacuum cleaner bag filter of claim 1, wherein the deodorizing sheet comprises a plurality of deodorizing sheets.

19. A vacuum cleaner bag filter comprising:
one or more filter walls forming a generally air permeable enclosure having a bag opening therethrough, the one or more filter walls having a working surface area through which air can pass during use;
a flange attached to the one or more filter walls to cover the bag opening, the flange comprising a relatively rigid structure having an air inlet passing into the air permeable enclosure;
a at least one deodorizing sheet attached to an inner surface of the one or more filter walls, and positioned on the one or more filter walls at a location opposite the air inlet, such that air entering the air inlet impinges upon the deodorizing sheet, the deodorizing sheet comprising:
a first sheet layer, and
a plurality of sodium bicarbonate particles operatively associated with the first sheet layer.

20. The vacuum cleaner bag filter of claim 19, wherein the deodorizing sheet further comprises a second sheet layer, and the plurality of sodium bicarbonate particles are generally deposited between the first sheet layer and the second sheet layer.

21. The vacuum cleaner bag filter of claim 20, wherein the sodium bicarbonate particles are adhered to at least the first sheet layer by a hot melt adhesive.

22. The vacuum cleaner bag filter of claim 20, wherein the sodium bicarbonate particles are non-uniformly distributed throughout the thickness of the deodorizing sheet.

23. The vacuum cleaner bag filter of claim 20, wherein the sodium bicarbonate particles are uniformly distributed throughout the thickness of the deodorizing sheet.

24. The vacuum cleaner bag filter of claim 20, wherein the first sheet comprises a non-woven sheet, and the second sheet comprises a scrim layer.

25. The vacuum cleaner bag filter of claim 24, wherein the sodium bicarbonate particles and second sheet layer are adhered to the first sheet layer by a hot melt adhesive.

26. The vacuum cleaner bag filter of claim 19, the deodorizing sheet further comprises a second sheet layer, the second sheet layer comprising an anti-penetration barrier to help prevent incoming objects from penetrating the one or more filter walls.

27. The vacuum cleaner bag filter of claim 19, wherein the deodorizing sheet covers less than about 30% of the working surface area.

28. The vacuum cleaner bag filter of claim 19, wherein the deodorizing sheet covers less than about 25% of the working surface area.

29. The vacuum cleaner bag filter of claim 19, wherein the deodorizing sheet covers about 4% to about 15% of the working surface area.

30. The vacuum cleaner bag filter of claim 19, wherein the deodorizing sheet is attached to the one or more filter walls by an air-impervious adhesive that covers at least about 5% of the surface area of the deodorizing sheet.

31. The vacuum cleaner bag filter of claim 19, further comprising an air restricting layer attached to the outer surface of the one or more filter walls and overlying the deodorizing sheet.

32. The vacuum cleaner bag filter of claim 31, wherein the air restricting layer comprises a blocking emulsion printed on the outer surface of the one or more filter walls.

33. The vacuum cleaner bag filter of claim 31, wherein the air restricting layer reduces airflow through the deodorant sheet by about 30% to about 90%.

34. The vacuum cleaner bag filter of claim 31, wherein the air restricting layer reduces airflow through the deodorant sheet by about 60-70%.

35. A vacuum cleaner bag filter comprising:
one or more filter walls forming a generally air permeable enclosure having a bag opening therethrough, the one or more filter walls having a working surface area through which air can pass during use;
a flange attached to the one or more filter walls to cover the bag opening, the flange comprising a relatively rigid structure having an air inlet passing into the air permeable enclosure;
one or more deodorizing sheets attached to an inner surface of the one or more filter walls, the one or more deodorizing sheets each comprising:
a first sheet layer, and
a plurality of sodium bicarbonate particles operatively associated with the first sheet layer; and
wherein the one or more deodorizing sheets are attached to the one or more filter walls by an air impermeable adhesive that covers at least about 5% of the total surface area of the one or more deodorizing sheets.

36. The vacuum cleaner bag filter of claim 35, wherein the one or more deodorizing sheets each further comprises a second sheet layer, and the plurality of sodium bicarbonate particles are generally deposited between the first sheet layer and the second sheet layer.

37. The vacuum cleaner bag filter of claim 36, wherein the sodium bicarbonate particles are adhered to at least the first sheet layer by a hot melt adhesive.

38. The vacuum cleaner bag filter of claim 36, wherein the sodium bicarbonate particles are non-uniformly distributed throughout the thicknesses of the one or more deodorizing sheets.

39. The vacuum cleaner bag filter of claim 36, wherein the sodium bicarbonate particles are uniformly distributed throughout the thicknesses of the one or more deodorizing sheets.

40. The vacuum cleaner bag filter of claim 36, wherein the first sheet comprises a non-woven sheet, and the second sheet comprises a scrim layer.

41. The vacuum cleaner bag filter of claim 40, wherein the sodium bicarbonate particles and second sheet layer are adhered to the first sheet layer by a hot melt adhesive.

42. The vacuum cleaner bag filter of claim 35, wherein at least one of the one or more deodorizing sheets is positioned on the one or more filter walls at a location opposite the air inlet, such that air entering the air inlet impinges upon the at least one deodorizing sheet.

43. The vacuum cleaner bag filter of claim 42, the at least one of the one or more deodorizing sheets further comprises a second sheet layer, the second sheet layer comprising an anti-penetration barrier to help prevent incoming objects from penetrating the one or more filter walls.

44. The vacuum cleaner bag filter of claim 35, wherein the one or more deodorizing sheets cover less than about 30% of the working surface area.

45. The vacuum cleaner bag filter of claim 35, wherein the one or more deodorizing sheets cover less than about 25% of the working surface area.

46. The vacuum cleaner bag filter of claim 35, wherein the one or more deodorizing sheets cover about 4% to about 15% of the working surface area.

47. The vacuum cleaner bag filter of claim 35, wherein the one or more deodorizing sheets are attached to the one or more filter walls by an air impermeable adhesive that covers about 5% to about 20% of the total surface area of the one or more deodorizing sheets.

48. The vacuum cleaner bag filter of claim 35, further comprising an air restricting layer attached to the outer surface of the one or more filter walls and overlying at least one of the one or more the deodorizing sheets.

49. The vacuum cleaner bag filter of claim 48, wherein the air restricting layer comprises a blocking emulsion printed on the outer surface of the one or more filter walls.

50. The vacuum cleaner bag filter of claim 48, wherein the air restricting layer reduces airflow through the at least one or the one or more deodorant sheets by about 30% to about 90%.

51. The vacuum cleaner bag filter of claim 48, wherein the air restricting layer reduces airflow through the at least one or the one or more deodorant sheets by about 60-70%.

52. The vacuum cleaner bag filter of claim 35, wherein the one or more deodorizing sheets comprises a single deodorizing sheet.

53. The vacuum cleaner bag filter of claim 35, wherein the one or more deodorizing sheets comprises a plurality of deodorizing sheets.

54. A vacuum cleaner filter comprising:
a generally air permeable filter having an upstream filter side and a downstream filter side, the filter being adapted to fit into a vacuum cleaner such that the upstream filter side faces an incoming air stream, and downstream filter side is opposite the upstream filter side;
a deodorizing sheet attached to the filter on at least one of the upstream filter side and the downstream filter side, the deodorizing sheet comprising:
a first sheet layer, and
a plurality of sodium bicarbonate particles operatively associated with the first sheet layer; and
wherein the deodorizing sheet is attached to the filter by an air impermeable adhesive that covers more than about 5% of the total surface area of the deodorizing sheet.

55. The vacuum cleaner filter of claim 54, wherein the filter comprises a pleated filter or a foam filter.

56. The vacuum cleaner filter of claim 54, wherein the filter comprises a cylindrical filter, a frustoconical filter, a conical filter, or a flat filter.

57. The vacuum cleaner filter of claim 54, wherein the deodorizing sheet further comprises a second sheet layer, and the plurality of sodium bicarbonate particles are generally deposited between the first sheet layer and the second sheet layer.

58. The vacuum cleaner filter of claim 57, wherein the sodium bicarbonate particles are adhered to at least the first sheet layer by a hot melt adhesive.

59. The vacuum cleaner filter of claim 57, wherein the first sheet comprises a non-woven sheet, and the second sheet comprises a scrim layer.

60. The vacuum cleaner filter of claim 54, wherein the deodorizing sheet is attached to the filter by an air impermeable adhesive that covers about 5% to about 20% of the total surface area of the deodorizing sheet.

61. The vacuum cleaner filter of claim 54, wherein the deodorizing sheet is attached to the upstream filter side.

62. The vacuum cleaner filter of claim 54, wherein the deodorizing sheet is attached to the downstream filter side.

63. The vacuum cleaner filter of claim 54, wherein the filter comprises a pre-motor filter, a post-motor filter, or a cyclone chamber filter.

* * * * *

UNITED STATES PATENT AND TRADEMARK OFFICE
CERTIFICATE OF CORRECTION

| | | |
|---|---|---|
| PATENT NO. | : 7,615,109 B2 | Page 1 of 1 |
| APPLICATION NO. | : 11/417167 | |
| DATED | : November 10, 2009 | |
| INVENTOR(S) | : Sepke et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 745 days.

Signed and Sealed this

Fourteenth Day of December, 2010

David J. Kappos
*Director of the United States Patent and Trademark Office*